(12) United States Patent
Gosselin et al.

(10) Patent No.: US 11,999,749 B2
(45) Date of Patent: Jun. 4, 2024

(54) SYNTHESIS OF A BIS-MESYLATE SALT OF 4-AMINO-N-(1-((3-CHLORO-2-FLUORO-PHENYL)AMINO)-6-METHYLISOQUINOLIN-5-YL)THIENO[3,2-D]PYRIMIDINE-7-CARBOXAMIDE AND INTERMEDIATES THERETO

(71) Applicants: Genentech, Inc., South San Francisco, CA (US); Hoffmann-La Roche Inc., Little Falls, NJ (US)

(72) Inventors: Francis Gosselin, San Mateo, CA (US); Stefan G. Koenig, San Francisco, CA (US); Eduardo V. Mercado-Marin, Escondido, CA (US); Andreas Stumpf, Dublin, CA (US); Daniel Zell, Belmont, CA (US); Haiming Zhang, San Mateo, CA (US); Stephan Bachmann, Allschwil (CH); Diane E. Carrera, Redwood City, CA (US); Michael E. Dalziel, Chicago, IL (US); Yonghui Ge, Suzhou (CN); Jie Zhang, Changzhou (CN); Raphael Bigler, Aargau (CH); Laure Elizabeth Simone Finet, Buschwiller (FR); Regis Jean Georges Mondiere, Basel (CH); Yuki Nakagawa, Toda (JP)

(73) Assignees: Genentech, Inc., South San Francisco, CA (US); Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/852,227

(22) Filed: Jun. 28, 2022

(65) Prior Publication Data
US 2023/0028651 A1    Jan. 26, 2023

(30) Foreign Application Priority Data
Jun. 30, 2021  (WO) ................ PCT/CN2021/103873

(51) Int. Cl.
*C07D 495/04*   (2006.01)
(52) U.S. Cl.
CPC ............................. *C07D 495/04* (2013.01)
(58) Field of Classification Search
CPC .................................................. C07D 495/04
See application file for complete search history.

(56) References Cited

U.S. PATENT DOCUMENTS

| 7,989,461 B2 | 8/2011 | DeMorin et al. |
| RE47,451 E | 6/2019 | Bae et al. |
| 2020/0308187 A1 | 10/2020 | Park et al. |

FOREIGN PATENT DOCUMENTS

| CN | 114213430 A | 3/2022 |
| WO | 2011/093684 A2 | 8/2011 |
| WO | WO 2013/100632 A1 * | 7/2013 |
| WO | 2014/003483 A1 | 1/2014 |
| WO | 2018/234343 A1 | 12/2018 |
| WO | 2022/089219 A1 | 5/2019 |
| WO | 2019/107987 A1 | 6/2019 |
| WO | WO 2019/107971 A1 * | 6/2019 |

OTHER PUBLICATIONS

Zell et al., An efficient second-generation manufacturing process for the pan-RAF inhibitor Belvarafenib, Organic Process Research & Development, 25, pp. 2338-2350 (2021).*
Hu, H., et al., "Design, synthesis and biological evaluation of novel thieno[3,2-d]pyrimidine and quinazoline derivatives as potent antitumor agents" Bioorg Chemistry (Epub: Jun. 26, 2019), 90:103086 (1-11) (Sep. 1, 2019).
Hung, H., et al., "1-(3,4,5-Trimethoxyphenyl)ethane-1,2-diyl esters, a novel compound class with potent chemoreversal activity" Bioorg Med Chem Lett 22(24):7726-7729 (Dec. 15, 2012).
"International Search Report—PCT/US2022/073195" (w/Written Opinion), :pp. 1-15 (dated Sep. 13, 2022).
Kim, Y., et al., "Synthesis and evaluation of thieno[3,2-d]pyrimidine derivatives as novel FMS inhibitors" Bioorg Med Chem Lett 29(2):271-275 (Jan. 15, 2019).
Lee, Ach, et al., "Thieno[3,2-d]pyrimidin-4(3H)-one derivatives as PDK1 inhibitors discovered by fragment-based screening" Bioorg Med Chem Lett (Epub: Apr. 25, 2012), 22(12):4023-4027 (Jun. 15, 2012).
Lee, S., et al., "(p40)2-Fc reduces immune-inflammatory response through the activation of T cells in collagen induced arthritis mice" Immunol Lett (Epub: May 23, 2016), 176:36-43 (Aug. 1, 2016).
Lim, S., et al., "Cobalt(III)-induced hexamerization of PEGylated insulin" Int J Biol Macromol (Epub: Aug. 3, 2011), 49(4):832-837 (Nov. 1, 2011).
Smith, A., et al., "Selective Inhibitors of the Mutant B-Raf Pathway: Discovery of a Potent and Orally Bioavailable Aminoisoquinoline" ACS J Med Chem 52(20):6189-6192 (Sep. 18, 2009).
Tan, Q., et al., "Synthesis and anticancer activities of thieno[3,2-d]pyrimidines as novel HDAC inhibitors" Bioorg Med Chem (Epub: Nov. 21, 2013), 22(1):358-365 (Jan. 1, 2014).

* cited by examiner

*Primary Examiner* — Deepak R Rao
(74) *Attorney, Agent, or Firm* — Genentech, Inc.; Richard G. A. Bone

(57) ABSTRACT

A manufacturing process to a bis-mesylate salt 1b of the pan-RAF inhibitor 4-amino-n-(1-((3-chloro-2-fluorophenyl)amino)-6-methylisoquinolin-5-yl)thieno[3,2-d]pyrimidine-7-carboxamide. The process features a number of efficient key reactions, including a robust and scalable Pd-catalyzed carbonylation reaction to generate thienopyrimidine 2 and a highly chemoselective Pt/V/C-catalyzed nitro group reduction to access penultimate intermediate 7. The final amide coupling of 7 and 2 was accomplished by a mild and safe protocol employing N,N,N',N'-tetramethylchloroformamidinium hexafluorophosphate (TCFH) as the coupling reagent, to produce a 1:1 adduct of the freebase and THF. The adduct afforded compound 1b with excellent yield, purity, and form stability on a multikilogram production scale after reaction with MsOH and recrystallization. The methods are able to produce a compound having upwards of 95% purity.

13 Claims, 9 Drawing Sheets

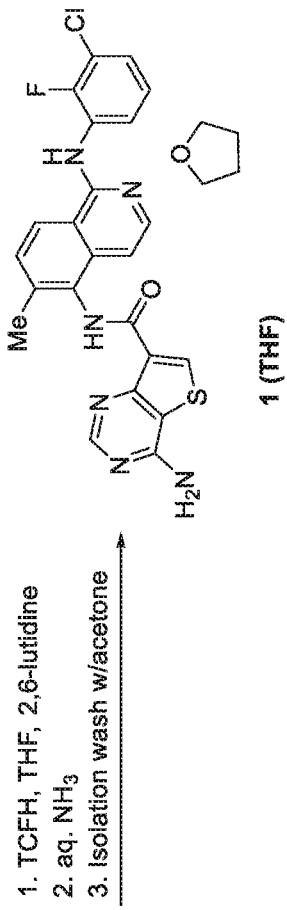
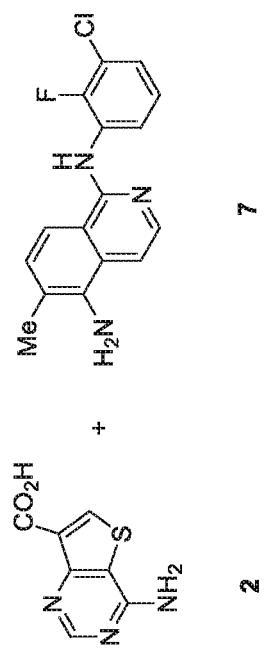
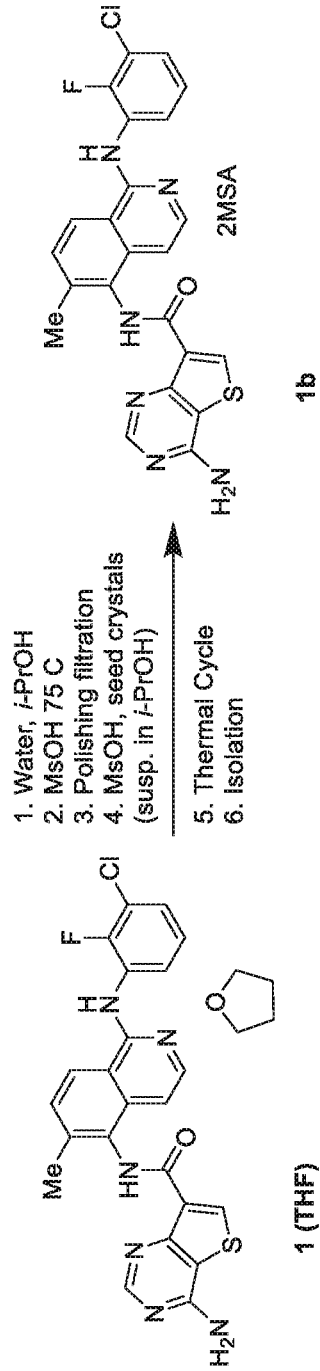
FIG. 10D
FIG. 10E

SYNTHESIS OF A BIS-MESYLATE SALT OF 4-AMINO-N-(1-((3-CHLORO-2-FLUORO-PHENYL)AMINO)-6-METHYLISOQUINOLIN-5-YL)THIENO[3,2-D]PYRIMIDINE-7-CARBOXAMIDE AND INTERMEDIATES THERETO

CROSS REFERENCE TO RELATED APPLICATIONS

This application claims priority under 35 U.S.C. § 119(a) to PCT/CN2021/103873, filed Jun. 30, 2021, which is incorporated herein by reference in its entirety.

TECHNICAL FIELD

The technology described herein generally relates to a synthesis, crystallization, and purification of a bis-mesylate salt of 4-amino-N-(1-((3-chloro-2-fluorophenyl)amino)-6-methylisoquinolin-5-yl)thieno[3,2-d]pyrimidine-7-carboxamide.

The technology more specifically relates to a synthesis and preparation at commercial scale, including certain intermediates.

BACKGROUND

4-Amino-N-(1-((3-chloro-2-fluorophenyl)amino)-6-methylisoquinolin-5-yl)thieno[3,2-d]pyrimidine-7-carboxamide (1) is a potent mitogen-activated protein kinase (MAPK) pathway inhibitor that has shown selective activity against advanced solid tumors that bear various RAS and RAF mutations (See, e.g., U.S. Pat. No. 9,156,852) and, in various salt forms, is currently undergoing clinical studies for several therapeutic indications.

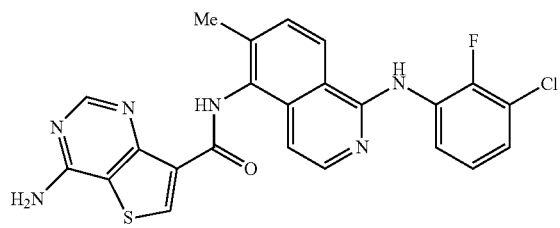

The MAPK pathway plays a crucial role in controlling cell growth and proliferation, and a number of different defects in this signal cascade are now understood to be the most significant origins of many human cancers. (See, e.g., Solit, D. B. et al., BRAF mutation predicts sensitivity to MEK inhibition, *Nature* 439, 358-362 (2006)) The RAF serine/threonine-protein kinase family is an important constituent of the MAPK pathway, and certain mutations in its A-, B- or C-RAF members lead to a dysregulation of signal transductions, which have been identified as a common cause of human cancers. (e.g., Yen, I., Shanahan, F., Lee, J. et al., *Nature* 594, 418-423 (2021)) In recent years, significant advancements in the selective inhibition of mutated RAF kinases have been achieved (e.g., Huestis, M. P., et al., *J. Med. Chem.* 2021, 64, 3940-3955; and Huestis, M. P., et al., *ACS Med. Chem. Lett.* (2021), DOI: 10.1021/acsmedchemlett.1c00063), though molecules that act as inhibitors of all three RAF members (so-called "pan-RAF" inhibitors), such as 1, have also become important.

Hitherto, 1 has been provided to patients in clinical trials as a bis-HCl (bis-hydrochloride) salt 1a, manufactured at scale according to the scheme in FIG. 1. However, both the bis-HCl salt and its prior method of production have significant drawbacks.

The process shown in FIG. 1 started with a nucleophilic aromatic substitution ($S_NAr$) reaction between 1-chloro-6-methyl-5-nitroisoquinoline 4 and 3-chloro-2-fluoroaniline 5 to yield intermediate, HCl salt 6a. The nitro-group of the organic moiety of 6a was then reduced in order to produce isoquinoline intermediate 7 (FIG. 1). The latter was then engaged in an amide coupling with thienopyrimidone 3 to produce penultimate intermediate 8. In this process, the pyrimidone moiety of 3 was converted in a one-pot procedure to the chloro-pyrimidine moiety in 8 using $POCl_3$ as both acid activator and chlorinating reagent. In the final step, 8 was aminated to generate the crude bis-hydrochloride salt 1a, which required extensive purification using a multi-step reslurry protocol.

The scheme of FIG. 1 has a number of significant limitations, including: a) the potential formation of impurities in several steps of the process, any of which would be problematic if present in trace amounts in a pharmaceutical end-product; b) the use of super-stoichiometric amounts of zinc for reduction of the nitro-group of 6a, which is both expensive and requires additional purification to remove excess metal; c) the need for multiple re-slurry purifications to remove impurities from the product of the amide coupling that produced intermediate 8, a consequence of which is solvent waste as well as overall lack of efficiency; d) the susceptibility of the chloropyrimidine intermediate 8 to a hydrolysis that substitutes the chloro group by a hydroxyl in the subsequent step; e) significant waste-production such as excess zinc arising from the reduction of 6a; and f) the lack of a reliable crystallization process by which to provide sufficient form and impurity control of the bis hydrochloride salt 1a, meaning that purification was extremely time consuming.

A different scheme to that of FIG. 1 has been presented (see, WO2013/100632) that utilizes 4-aminothieno[3,2-d]pyrimidine-7-carboxylic acid in place of thienopyrimidone 3 also has drawbacks associated with production of the bis-HCl salt.

Specifically, use and production of the bis-hydrochloride salt form 1a was associated with several practical difficulties. First, it was very difficult to control the stoichiometry of hydrochloric acid at elevated temperatures due to evaporation, which meant that the final product frequently contained a hydrolysis impurity (arising from hydrolysis of the amino group of 1). This problem could not be straightforwardly addressed by use of excess HCl due to the hydrolysis and because the product 1a itself was still capable of disproportionating on handling (to a mix of free base 1, and mono-HCl and di-HCl salts thereof). Second, there are safety concerns associated with use of mineral acids at scale, given that excess amounts of the acids need to be properly quenched after their use in a reaction, which itself could give rise to an unwanted exothermic neutralization step in the work-up procedure; these concerns are particularly acute with HCl. Third, the hygroscopicity of the bis-hydrochloride salt 1a complicated the control of water content in the product. Fourth, the particle size distribution (PSD) of the bis-HCl salt was both hard to control and routinely led to clogging of filters, thereby resulting in exceptionally long filtration times during purification. Consequently, the salt needs to be milled in order to produce uniformly sized particles.

Accordingly, there is a need for an efficient multi-kilogram manufacturing process to supply ongoing clinical studies that use the therapeutic agent 1, as well as to provide a process suitable for supplying commercial product.

The discussion of the background herein is included to explain the context of the technology. This is not to be taken as an admission that any of the material referred to was published, known, or part of the common general knowledge as at the priority date of any of the claims found appended hereto.

Throughout the description and claims of the instant application the word "comprise" and variations thereof, such as "comprising" and "comprises", is not intended to exclude other additives, components, integers or steps.

SUMMARY

The instant disclosure addresses the synthesis of 4-amino-N-(1-((3-chloro-2-fluorophenyl)amino)-6-methylisoquinolin-5-yl)thieno[3,2-d]pyrimidine-7-carboxamide (1), in particular its bis-mesylate (variously denoted "2MsA", "2MSA", or "2MsOH") salt form (1b), and particularly at high purity and at a commercial scale, suitable for tableting and delivery in pharmaceutical compositions.

A method, shown in outline in FIG. 2, of synthesizing a compound of formula 1b,

1b the method comprising: reacting compound 4 with compound 5a in the presence of a solvent such as methyl ethyl ketone (MEK, 2-butanone), or methyl isobutyl ketone (MIBK) with an organic base such as NEt₃, to produce compound 6a;

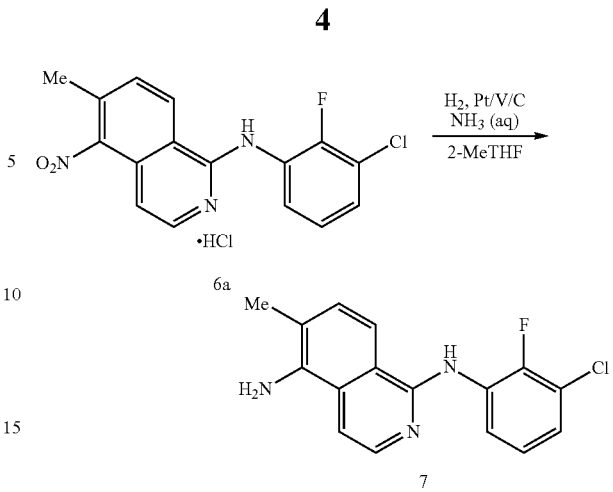

coupling compound 7 with compound 2 using N,N,N',N'-tetramethylchloroformamidinium hexafluorophosphate (TCFH), 2,6-lutidine, in N-methyl-pyrrolidine, followed by dissolution with an aqueous mixture of methanesulfonic acid (MsOH) in N-methyl pyrrolidine, to provide a crude form of 1b;

2

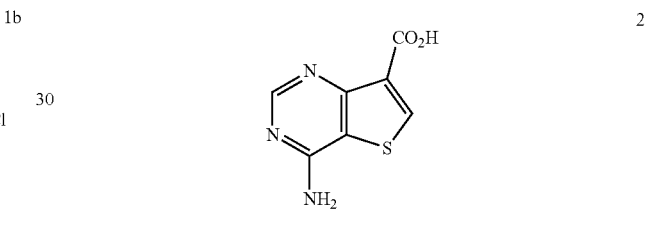

and purifying the crude form of 1b by recrystallization with MsOH in DMSO and water.

The method of making 1b herein is capable of providing product at a purity of >99 A % HPLC.

The method of making 1b further includes a method, as shown in FIG. 3, wherein compound 2 is prepared by a process comprising regioselective bromination of 22 to produce 23;

chlorinating 23 to form 24;

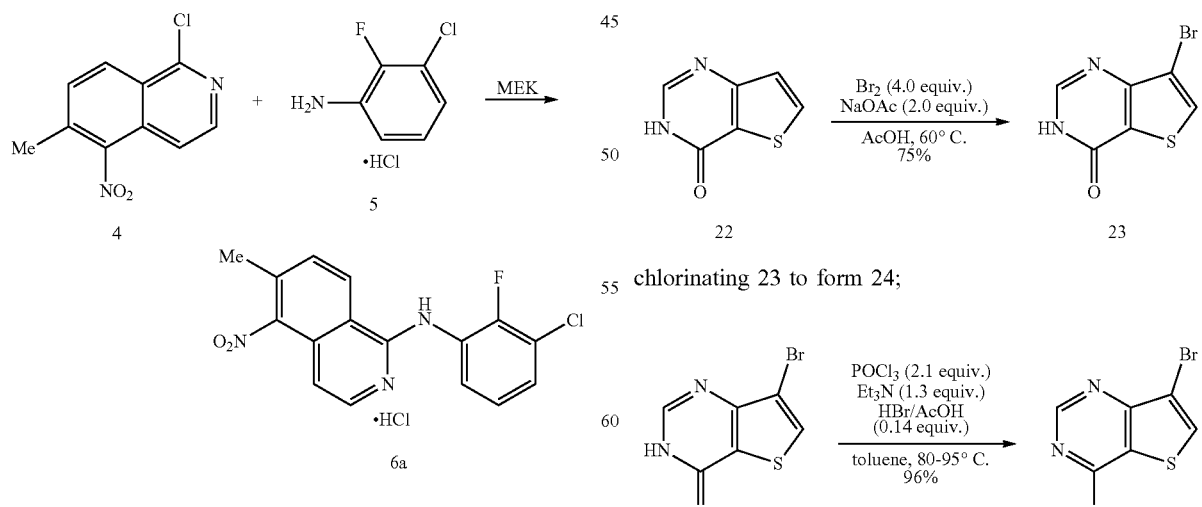

converting 24 to a protected compound 25;

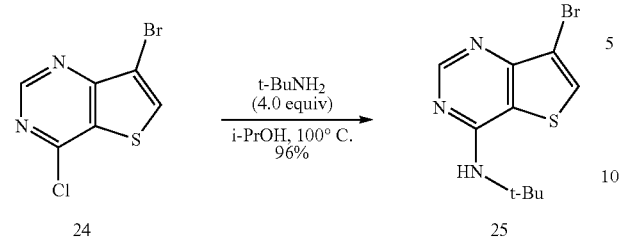

carbonylation of 25 to form 26;

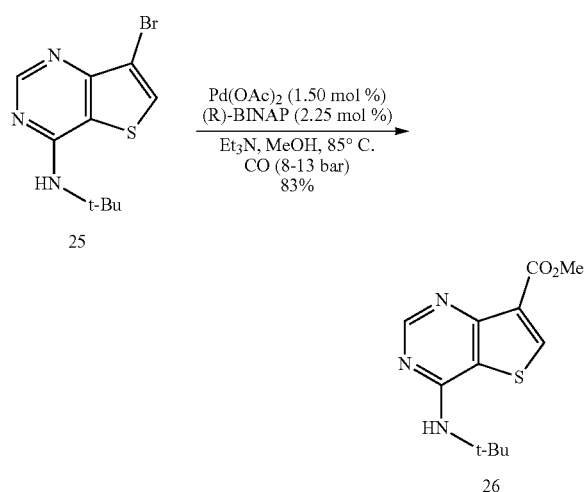

and deprotecting 26 with acid, then base, followed by neutralization with an acid such as acetic acid to provide compound 2.

The method of making 1b further includes a method, shown in FIG. 4, wherein compound 4 is prepared by a process comprising selectively methylating 5-nitroisoquinoline to produce 42;

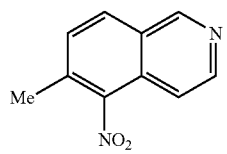

oxidizing 42 to produce 43;

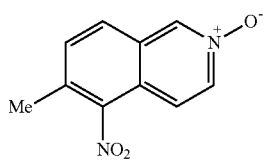

and chlorinating 43 to produce 4.

The method of making compound 1b further includes a method, as shown in FIG. 5, in which compound 5a is prepared by a process comprising regioselectively fluorinating 50 to produce 51;

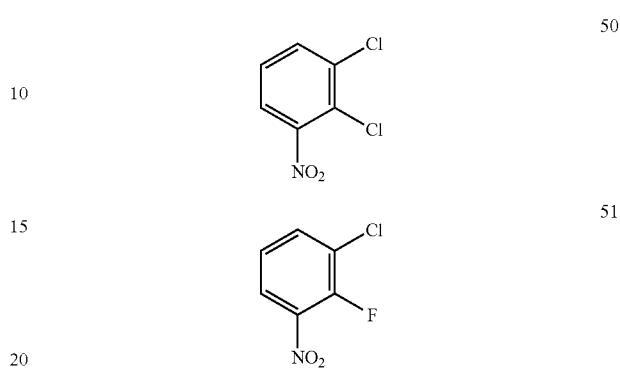

and catalytically reducing 51 with $H_2$ over Raney-Nickel to produce 5a, wherein the fluorinating and reducing occur in the same reaction vessel without separating compound 51 between each step.

The disclosure further includes a method of making compound 2 as further described herein.

The disclosure further includes a method of producing a compound of formula 1b, comprising coupling a compound of formula 7 with a compound of formula 2,

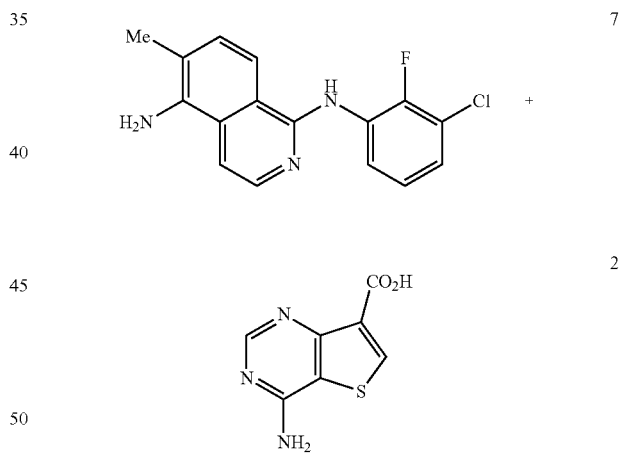

utilizing 2,6-lutidine and TCFH in N-methyl pyrrolidine, followed by washing in methanesulfonic acid in N-methyl pyrrolidine, to produce a crude 1b, which further needs to be purified and recrystallized.

The disclosure further includes a method of producing a compound of formula 1b, comprising coupling a compound of formula 7 with a compound of formula 2, utilizing 2,6-lutidine and TCFH in aqueous ammonia, followed by washing in acetone to produce a 1:1 adduct of THF and 1. Compound 1b can be produced in pure form by washing the adduct with methanesulfonic acid in isopropanol.

The disclosure further includes a compound of formula 26, and methods of making the same.

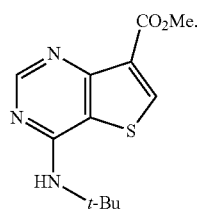

The disclosure further includes the (1:1) adduct of THF and 4-amino-N-(1-((3-chloro-2-fluorophenyl)amino)-6-methylisoquinolin-5-yl)thieno[3,2-d]pyrimidine-7-carboxamide, tetrahydrofuran, and crystalline forms thereof.

BRIEF DESCRIPTION OF THE DRAWINGS

FIG. 4 shows a process to isoquinoline starting material 4;
and
FIG. 5 shows a process to aniline starting material 5a.
FIG. 6 shows processes for production of intermediate 6a.
FIG. 7 shows HTE screening of the chemoselective nitro reduction of freebase 6.
FIG. 8. One-step nitro reduction process.
FIG. 9: Final two-step manufacturing process for nitro group reduction of 6a.
FIG. 10D: Amide coupling to produce a THF adduct of 1.
FIG. 10E: Conversion of THF adduct of 1 to the di-MSA salt, 1b.

DETAILED DESCRIPTION

Figure 1:
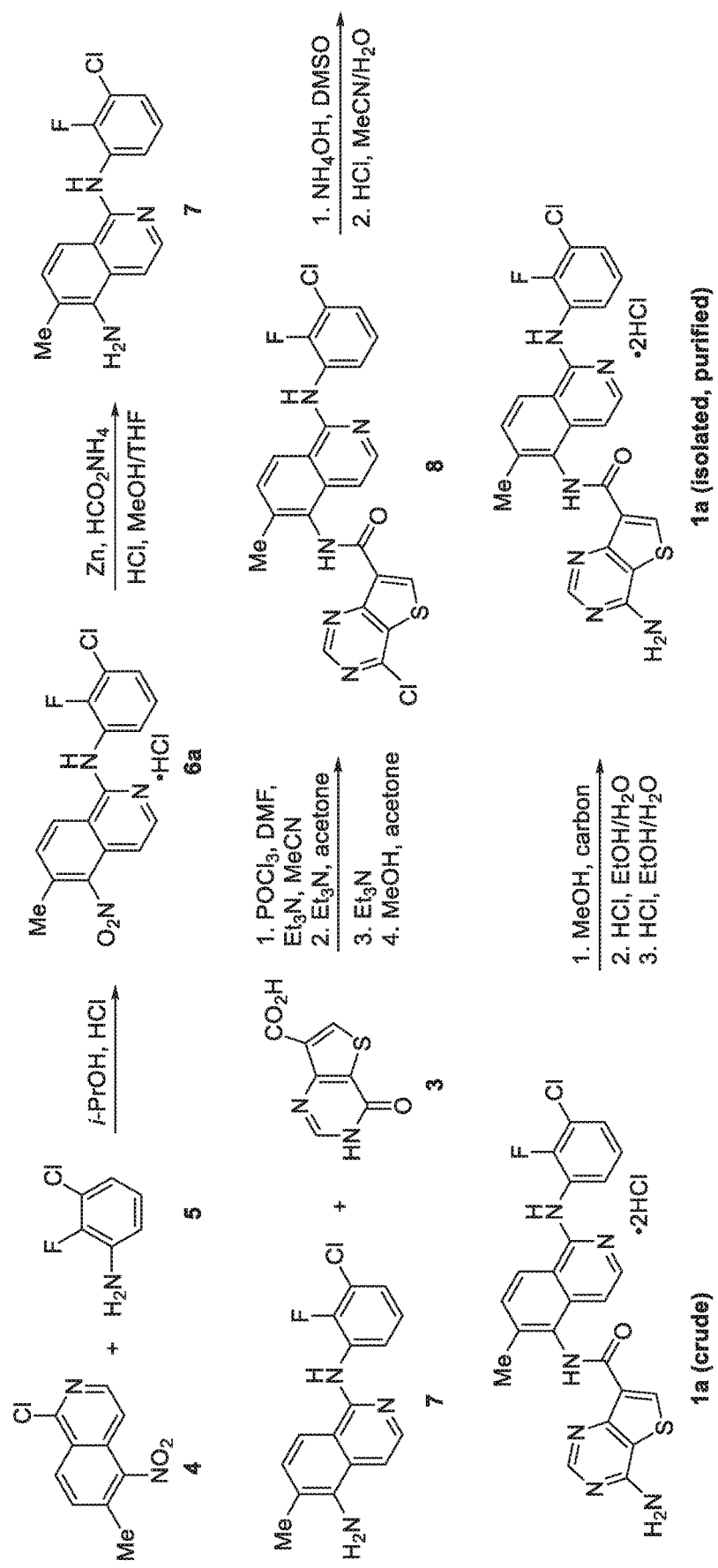
FIG. 1 shows a flow-chart of a process as disclosed in the prior art and further distinguished herein.

Reference will now be made in detail to certain embodiments of the process, examples of which are illustrated in the accompanying structures and formulas. While the process will be described in conjunction with the enumerated embodiments, it will be understood that they are not intended to limit the invention to those embodiments. On the contrary, the process is intended to cover all alternatives, modifications, and equivalents which may be included within the scope of the process as defined by the claims. One skilled in the art will recognize many methods and materials similar or equivalent to those described herein, which could be used in the practice of the present process. Accordingly, the present process is in no way limited to the methods and materials described. In the event that one or more of the incorporated literature, patents, and similar materials differs from or contradicts this application, including but not limited to defined terms, term usage, described techniques, or the like, this application controls.

Definitions

Unless otherwise defined, all technical and scientific terms used herein have the same meaning as commonly understood by one of ordinary skill in the art to which this invention belongs. The nomenclature used in this application is based on the *ACS Style Guide and The Journal of Organic Chemistry* list of "Standard Abbreviations and Acronyms" (both published by the American Chemical Society, Washington, D.C.), as well as on IUPAC systematic nomenclature, unless indicated otherwise.

Chemical elements are identified in accordance with the Periodic Table of the Elements, CAS version, Handbook of Chemistry and Physics, 75th Ed., and later.

The compounds herein include respective geometric (or conformational) isomeric forms of a given structure except where the structure in question is otherwise intended to be limited. For example, the Z and E double bond isomers, as well as geometric (or conformational) mixtures of isomers are included.

It is to be understood that when a compound or Example herein is shown as a specific salt, the corresponding free-base, as well as other salts of the corresponding free-base (including pharmaceutically acceptable salts of the corresponding free-base) are contemplated, except where it is clear that a specific salt or the free base itself is referenced.

Unless otherwise stated, all tautomeric forms of structures depicted herein are also included. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Unless otherwise stated, structures depicted herein are also meant to include compounds that differ only in the presence of one or more isotopically enriched atoms in addition to any isotopically enriched atom that has been explicitly identified. For example, compounds, wherein the independent replacement or enrichment of one or more hydrogen atoms by a deuterium or a tritium, carbon by $^{13}C$ or $^{14}C$, nitrogen by $^{15}N$, sulfur by $^{33}S$, $^{34}S$ or $^{36}S$, oxygen by $^{17}O$ or $^{18}O$, or fluorine by $^{18}F$ are included. Such isotopically enriched compounds are useful, for example, as analytical tools, as probes in biological assays, or as therapeutic agents.

As between chemical names listed and structures shown herein, if there are any discrepancies, the structure prevails.

The assay value indicates how much of a final material actually contains the desired product in weight. For example, 98% assay or 98% weight assay means that in the isolated material, 98% of the desired product based on its weight was obtained. This measure can be superior to HPLC A % in terms of accurately determining the presence of impurities because some impurities are UV-inactive and thus do not show up in an HPLC analysis. Weight assay, in contrast, captures the impact of all impurities, including inorganic material and residual quantities of solvents.

As used herein, "a" or "an" means one or more, unless clearly indicated otherwise.

Overview

Figure 2:
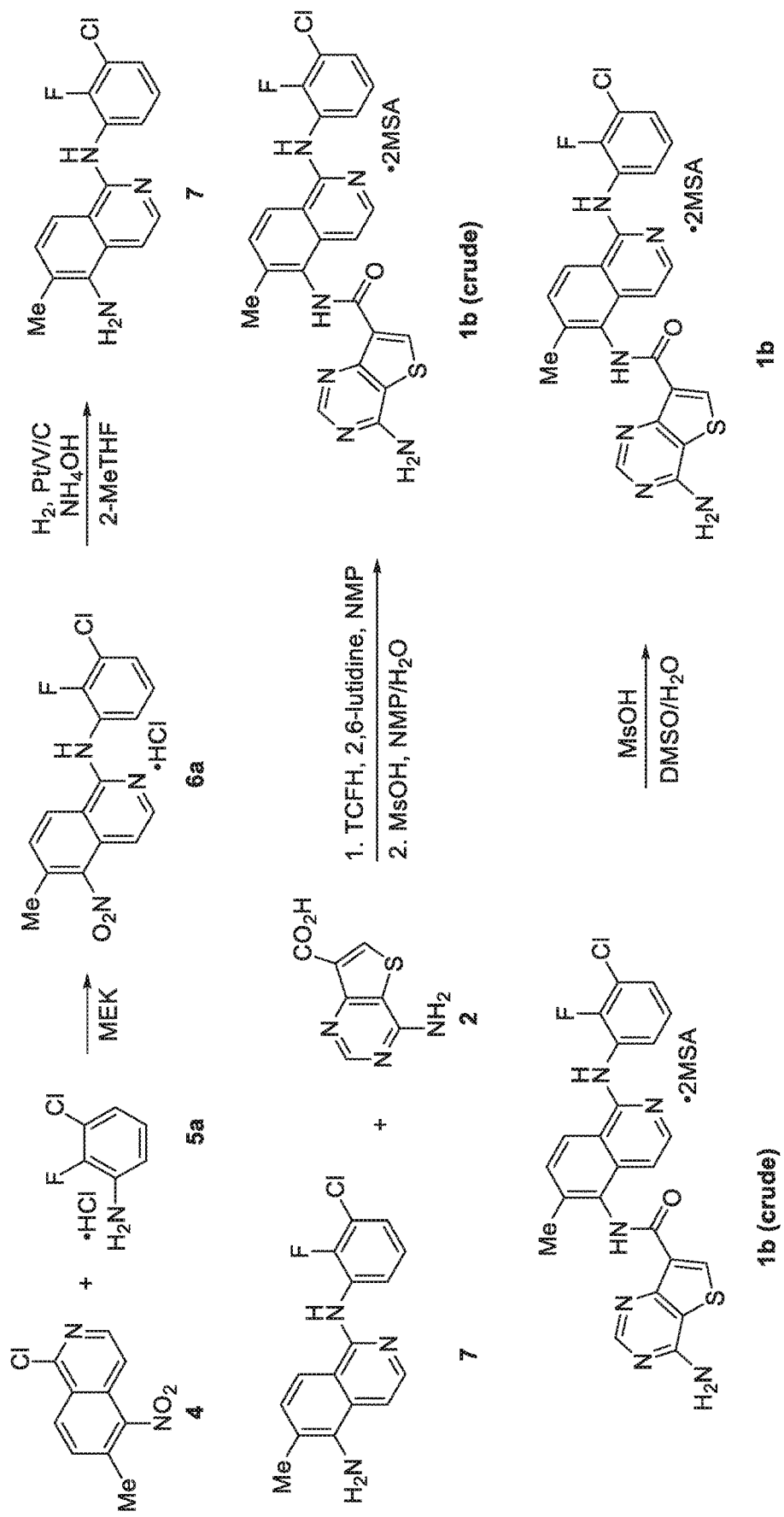
FIG. 2 shows a second flow-chart of a process as described herein.

Due to the numerous limitations of the above-described route to the bis-HCl salt of 1, a new route to a bis-mesylate salt of 1, which would fully meet the demands of a clinical phase supply, was developed. An overview of this new approach, which is an enhanced efficiency synthesis overall, is depicted in FIG. 2. Key advantages, benefits, and improvements of the process of FIG. 2 include, but are not limited to, the following.

Starting material 3-chloro-2-fluoroaniline 5 is employed as its hydrochloride salt 5a, which improves the yield of the S$_N$Ar reaction with 4 by leveraging the capability of the hydrochloric acid already present in the salt to act as a catalyst for the step. Additionally, the HCl salt 5a is a solid and thus easier to handle and purify than its freebase counterpart, which is an oil.

The reagents for achieving the reduction of the nitro group in 6 are a highly chemoselective Pt/V/C-catalyzed hydrogenation protocol, which afforded isoquinoline 7 more efficiently than the use of Zinc as the reductant as in FIG. 1.

A new amide coupling step based on mild reaction conditions, which differs from the prior process of FIG. 1 in two principal ways, is used. First, the use of highly reactive and corrosive POCl$_3$ was avoided. Second, to specifically address the problems associated with the instability of the chloro-pyrimidine intermediate 8 and the low step-economy of one of the prior processes (FIG. 1), an already aminated starting material, thienopyrimidine 2, is used in place of thienopyrimidone 3. The use of 2 as a starting material has two benefits: it already contains the desired amino group thereby obviating the need to introduce that group at this stage, as was done when using the alternate starting material, pyrimidone 3; and it enables the crude bis-mesylate form of 1 to be obtained directly from coupling of the intermediate 7 with 2, thereby simultaneously improving the step-economy of the process and avoiding the generation of undesirable impurities.

Isolating the active moiety as the bis-mesylate salt (1b), represents a further significant change relative to prior processes. The bis-mesylate form of 1 offers several superior physical properties relative to the 2HCl salt.

First, its lower hygroscopicity means that its weight assay value is more reliably measured and controlled, and also facilitates control over the stoichiometry of methanesulfonic acid during the isolation and recrystallization steps.

Second, the bis-mesylate provides more stable form control (where the form is the crystal lattice, such as defined by space group and unit cell parameters), which thereby offers better reliability of the selected form.

Third, the bis-mesylate salt also provides control over particle size distribution of the final product in a way that shortens filtration time and further obviates the need for wet milling of the solid particles. (The salt may be dry milled, such as by impact milling or jet milling, after isolation and drying of the material.)

Synthesis of Starting Materials 4-aminothieno[3,2-d]pyrimidine-7-carboxylic acid (2)

Figure 3:
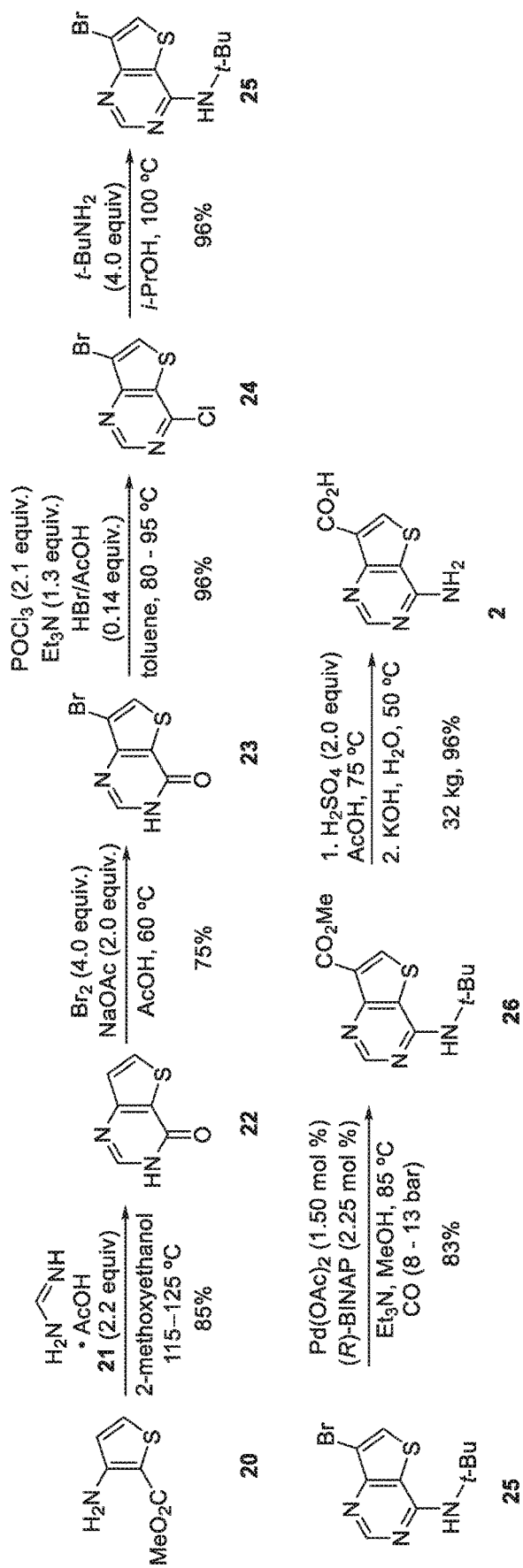
FIG. 3 shows a manufacturing process to thienopyrimidine starting material 2.

In order to obtain an efficient and scalable process to the thienopyrimidine starting material 2 (for which there are no practical published syntheses), the main focus was placed on achieving a step-economical route that circumvents unnecessary manipulations late in the process. Extensive optimization culminated in a six-step process, shown in FIG. 3, which can provide the thienopyrimidine 2 in an overall yield of 47% and >99.5 A % HPLC purity on a multi-kilogram scale.

The process to 2 commences with the construction of the thienopyrimidone core by reacting commercially-available methyl 3-aminothiophene-2-carboxylate (20) with formamidine acetate (21) to provide thienopyrimidone 22. This reaction can result in 22 at an 85% yield on a multi-kilogram production scale.

In order to selectively introduce the carboxylic acid moiety that appears in the 7-position of thienopyrimidine 2, a reaction sequence involving regioselective bromination and Pd-catalyzed carbonylation (see, e.g., Barnard, C. F. J., Palladium-Catalyzed Carbonylation—A Reaction Come of Age, *Organometallics*, (2008), 27, 5402-5422, and Brennführer, A.; Neumann, H.; Beller, M., Palladium-catalyzed carbonylation reactions of aryl halides and related compounds, *Angew. Chem. Int. Ed.*, 2009, 48, 4114-4133) is utilized.

With regard to bromination of thienopyrimidone 22, unoptimized conditions resulted in undesirable di-brominated products. To overcome this, sodium acetate is employed as a buffer to guard against the hydrobromic acid side-product, which can improve the yield of 23 to 75% and reduce the di-brominated impurity to less than 2 A % HPLC. It would be understood by those skilled in the art that the influence of the hydrobromic acid side-product could be diminished by use of bases other than sodium acetate.

Subsequently, a chlorination reaction with POCl$_3$, to produce 24, followed by an amination reaction, can give rise to the key intermediate 25 in 96% yield for each step. It would be understood by those skilled in the art that alternative chlorination agents can provide 25 from 24 in acceptable yields.

An important step of this synthesis of 2 is the development of a powerful and scalable catalytic system for the carbonylation of the nitrogen-rich, and thus challenging, intermediate 25. A high-throughput-experimentation (HTE) screening for the Pd-catalyzed carbonylation step revealed that (S)-2,2'-bis(diphenylphosphino)-1,1'-binaphthalene ((S)-BINAP) outcompeted other ligands among a series of selected mono- and bidentate phosphines. (See, e.g., Albaneze-Walker, J.; Bazaral, C.; Leavey, T.; Dormer, P. G.; Murry, J. A., Improved carbonylation of heterocyclic chlorides and electronically challenging aryl bromides, *Org. Lett.*, (2004), 6, 2097-2100.) In practice, either (R) or (S) form of BINAP suffices. An optimization of other reaction conditions established that a combination of 1.50 mol. % Pd(OAc)$_2$ and 2.25 mol. % (R)-BINAP is a preferred catalytic system. By using triethylamine as the accompanying base and methanol as the solvent, the intermediate 26 can be produced in a yield of 83%. It would be understood by one of skill in the art that other combinations of catalyst and ligand, as well as other ratios of Pd and BINAP, and/or other solvents and accompanying bases, can achieve acceptable yields and efficiencies of production of 26.

In the final step of deprotecting 26, the low solubility and zwitterionic nature of the thienopyrimidine product 2 remained problematic for developing an efficient purification method. An adjustment to mild acidic pH, such as pH=5, in the work-up procedure was performed to ensure that impurities were efficiently purged. After implementation of these changes, the intermediate 2 is produced with a yield of 96% on 32 kg scale. It would be understood by one skilled in the art that a range of conditions as well as choice of alkali reagent can be deployed to effect this deprotection step.

1-Chloro-6-methyl-5-nitroisoquinoline (4)

Figures 4, 5:
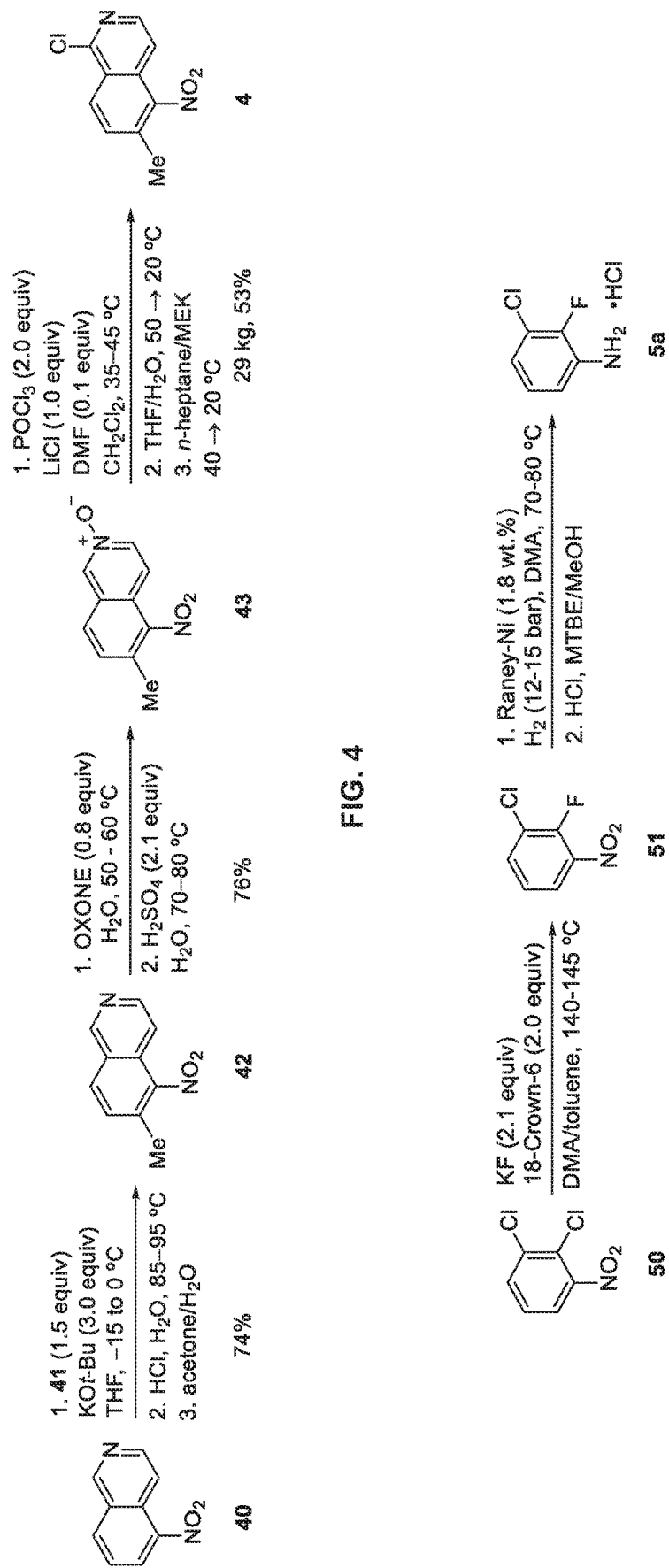

An exemplary process to the functionalized isoquinoline starting material 4 (1-chloro-6-methyl-5-nitroisoquinoline, which is not commercially available) is shown in FIG. 4. Other methods of making 4 are known to, or can be devised by, those of skill in the art.

The process of FIG. 4 was initiated by subjecting 5-nitroisoquinoline 40 to a vicarious nucleophilic substitution reaction (see e.g., Makosza, M.; Winiarski, J., Vicarious nucleophilic substitution of hydrogen, *Acc. Chem. Res.*, 1987, 20, 282-289) wherein the chloride on ethyl-2-chloroacetate (41), whose anion is the nucleophile, acts as a concurrent leaving group, to generate the methylated intermediate 42. Advantageously, this reaction can be carried out in a one-pot sequence comprising three steps.

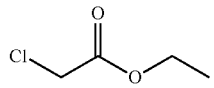

41

Starting with the actual nucleophilic substitution, subsequent decarboxylation and final crystallization from an acetone/water solvent mixture can deliver intermediate 42 in 74% overall yield. The reaction can provide a regioselectivity of >99:1 over an unwanted isomer obtained by nucleophilic substitution occurring para to the nitro-group.

In the subsequent step, the N-oxide 43 is afforded with 76% yield on multi-kilogram scale by employing OXONE® (the triple salt, 2KHSO$_5$·KHSO$_4$·K$_2$SO$_4$) as an environmentally-safe, inexpensive, and scalable oxidant. (See, e.g., Hussain, H.; Green, I. R.; Ahmed, I., Journey describing applications of oxone in synthetic chemistry, *Chem. Rev.*, (2013), 113, 3329-3371.) It would be understood by those skilled in the art that other oxidants are available and effective to achieve the oxidation to N-oxide 43.

Finally (FIG. 4), a highly regioselective chlorination of intermediate 43 produces 4. Preferred conditions use POCl$_3$ and lithium chloride in a DMF/dichloromethane solvent system, but one of skill in the art would appreciate that alternative chlorinating agents and/or solvents can accomplish the same transformation. Product 4 can be isolated from the reaction mixture by solvent extraction and recrystallization. In one instance of deploying the preferred conditions of FIG. 4, 29 kg of 4 were produced in 53% yield after isolation from THF/water and recrystallization from n-heptane/methyl-ethyl ketone (MEK).

3-Chloro-2-fluoroaniline hydrochloride (5

Starting material 5 is commercially available but samples typically contain undesirable quantities of regio-isomer impurities. An exemplary process to the HCl salt, 5a (3-chloro-2-fluoroaniline hydrochloride) is shown in FIG. 5. It would be further understood that one of skill in the art would be able to devise other synthetic routes to a form of 5 that is acceptably pure for use in a scaled up process for manufacturing a pharmaceutical composition.

In a first step (a nucleophilic substitution, FIG. 5), commercially available 1,2-dichloro-3-nitrobenzene (50) is converted to an intermediate fluoride 51 using KF as fluorination reagent in a dimethyl acetamide/toluene mixture as solvent, preferably with two molar equivalents of 18-crown-6 ligand to scavenge excess potassium, though alternative fluorinating and chelating agents, as known to those skilled in the art, could also be used. This step is efficient due to the high concentration of free fluoride anion.

In a telescoped process (in which 51 is not separated before the subsequent reduction step), hydrogenation utilizing Raney-nickel as the catalyst can reduce the nitro group in 51 to a corresponding amino group in 5a. Notwithstanding the fact that other suitable choices of catalyst can be chosen for this step, it is noteworthy that Pt/C as the catalyst was found to be much less chemo-selective than Raney-nickel, and resulted in significant levels of the undesired hydrodechlorination side product.

The corresponding product 3-chloro-2-fluoroaniline hydrochloride (5a) can be liberated from the catalyst system by acid in a suitable solvent. For example, after treatment with hydrochloric acid in methyl tert-butyl ether (MTBE) and methanol, the product 5a was generated in 35% overall yield over the three steps shown in FIG. 5 (fluorination, followed by reduction and salt formation), on 100 kg scale.

Synthesis of a bis-mesylate salt of 4-amino-N-(1-((3-chloro-2-fluorophenyl)amino)-6-methylisoquinolin-5-yl)thieno[3,2-d]pyrimidine-7-carboxamide As described by way of specific synthetic schemes in the Examples that follow, the disclosure comprises a method of synthesizing a compound 1 and its bis-mesylate salt, 1b, and intermediates thereto.

S$_N$Ar Reaction

Figures 6, 7:
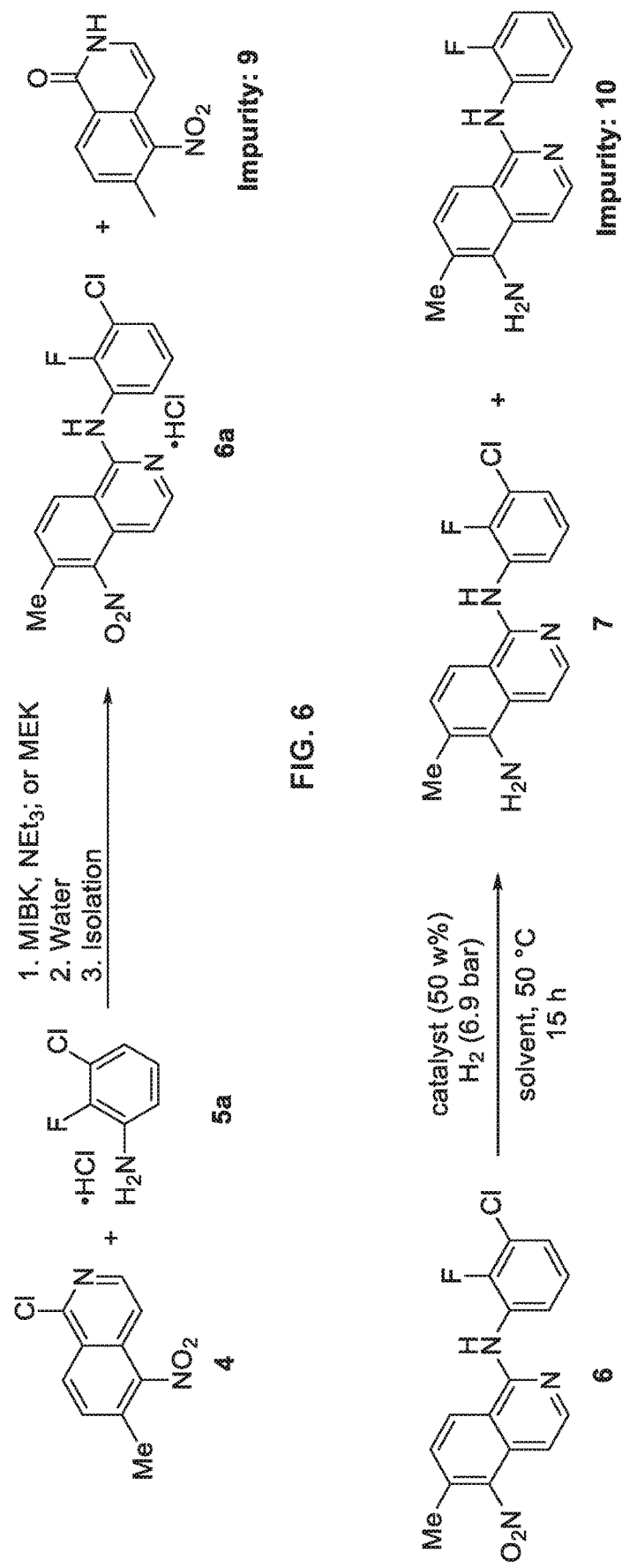

Making efficient at scale the S$_N$Ar reaction of 1-chloro-6-methyl-5-nitroisoquinoline 4 and 3-chloro-2-fluoroaniline hydrochloride 5a to produce hydrochloride salt 6a, depicted in FIG. 6, required several optimizations. The optimizations improved the following several major drawbacks of a comparable step of the prior art, in FIG. 1, as well as other published descriptions of similar interconversions (cf. Smith, et al., Selective Inhibitors of the Mutant B-Raf Pathway: Discovery of a Potent and Orally Bioavailable Aminoisoquinoline, *J. Med. Chem.*, (2009), 52: 6189-6192). Harsh reflux conditions had led to the loss of volatile hydrochloric acid during the conditions employed in the reaction of FIG. 1, and had led to irreproducibility across batches. Additionally, a persistent impurity, 6-methyl-5-nitroisoquinolin-1(2H)-one 9, was formed by hydrolysis of 4 at elevated temperature. And finally, the reaction conditions of the process step shown in FIG. 1, specifically the use of isopropanol as a solvent, favored generation of the unwanted GTI isopropyl chloride. Because the isopropyl chloride was typically formed late in the duration of the reaction, it was not easy to remove it from the product, and so minimizing its production throughout the course of the reaction is desirable. Even 0.5 wt. % by proportion of isopropyl chloride in the product is an undesirable fraction for a pharmaceutical grade process.

A screening of solvents for an alternative medium to isopropanol, in order to avoid the possibility of creating genotoxic impurity isopropyl chloride, indicated that methyl ethyl ketone (MEK) could be utilized without compromising efficiency of the conversion. It would be understood by those skilled in the art, however, that still other solvents could be deployed to similarly advantageous effect. Such other solvents include, but are not limited to, iso-propanol, acetonitrile, propionitrile, methyl isopropyl ketone, methyl isobutyl ketone (MIBK), Me-THF, 1,4-dioxane, toluene, dimethyl carbonate, trifluoroethanol, and DMSO. Preferred solvents include MEK, methyl isopropyl ketone, MIBK, trifluoroethanol, acetonitrile, and propionitrile. Most preferred solvents include MEK, MIBK, and trifluoroethanol.

The aniline starting material 5 can be deployed as its easier-to-handle hydrochloride salt 5a, which is an anhydrous solid, instead of a free base in conjunction with HCl as a reagent in an aqueous or protic solvent.

These two changes (to starting material and solvent) significantly raised the overall reproducibility of this step, and also avoided the uncontrolled formation of the isoquinolinone impurity 9 by both ensuring that a defined amount of hydrochloric acid (1 molar equivalent) is present during the reaction, and by reducing the water content in the aniline. Additionally, the presence of hydrochloric acid in starting material 5a has actually been found to be advantageous for reactivity, a fact which can be attributed to its probable catalytic activity in this $S_NAr$ reaction. (See, e.g., De Rosa, M.; Arnold, D.; Hartline, D., Four Mechanisms in the Reactions of 3-Aminopyrrole with 1,3,5-Triazines: Inverse Electron Demand Diels-Alder Cycloadditions vs. $S_NAr$ Reactions via Uncatalyzed and Acid-Catalyzed Pathways, J. Org. Chem., (2013), 78, 8614-8623.)

Additionally, several bases were screened to improve reaction efficiency, including: 1,8-diazabicyclo[5.4.0]undec-7-ene (DBU), $NEt_3$, 1,5-diazabicyclo[4.3.0]non-5-ene (DBN), $NBu_3$, N-methyl morpholine, Hünig's base, 4-dimethylaminopyridine (DMAP), N-methyl imidazole, and 1,4-diazabicyclo[2.2. 2]octane (DABCO). Of these, preferred bases include: $NEt_3$ and $NBu_3$, of which the most preferred is $NEt_3$. The typical stoichiometry of the base is less than 2.0 eq., where the preferred range is 0.5-1.0 eq., and the most preferred is 0.8-1.0 eq. (A concentrated acid in the reaction mixture is important for the reaction kinetics. But HCl is highly volatile, and therefore may be lost during the course of the reaction. Such loss can be mitigated by using an organic base, which can trap the HCl, but the base must be deployed in conservative quantities, as an excess amount of base can quench the reaction. Additionally, the presence of base serves to avoid corrosion issues during the drying of the wet cake of compound 6a.)

Effective temperature ranges for the reaction are 70-110° C., and for MIBK as a solvent, the preferred temperature is 105° C. For other solvents, the preferred temperature is typically 5-10° C. below its respective boiling point.

During the process of purification of 6a, up to 10% of residual aniline hydrochloride 5a was initially detected when crystallizing the product 6a directly from the reaction mixture. Fortunately, this impurity can be efficiently purged by adding water to increase its solubility in MEK or MIBK, as applicable (not shown in FIG. 6).

With such process improvements, and as further described in Example 11a herein, intermediate 6a can be generated in 88% yield and 99.9 A % HPLC purity (FIG. 6), at a scale of 56 kg where MEK is used.

As a practical matter, compound 6, which is needed for the subsequent step in the synthesis of 1b described herein, is easier to isolate and purify as its HCl salt 6a than as a free base, due to the fact that it crystallizes from solution more readily.

Nitro Group Reduction of 6

The freebase of 6a, which is used in the next step, can be obtained from 6a in more than one way.

Figures 8, 9:
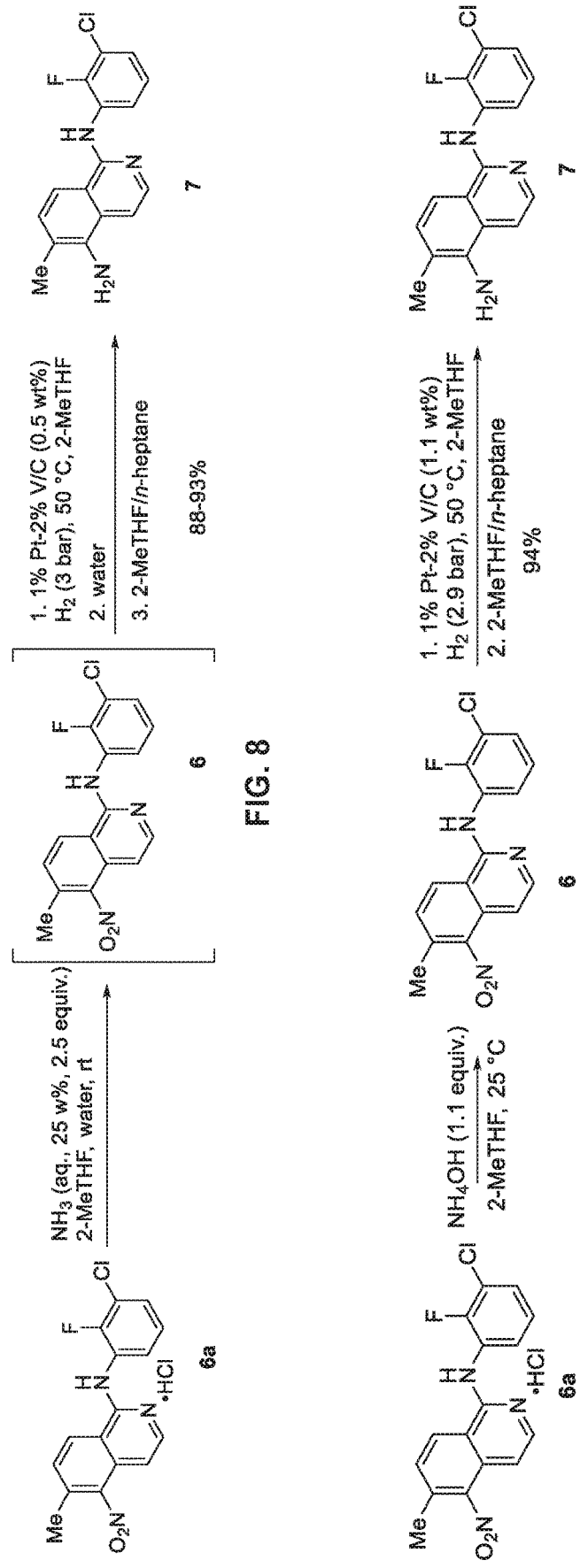

For example, as shown in FIG. 8, obtaining free base 6 from 6a was achieved using $NH_4OH$ as a base in a one-pot process with the subsequent hydrogenation. The corresponding step can also be achieved in a two-step process, with hydrogenation following isolation of 6 (see FIG. 9). In light of the drawbacks associated with the zinc-mediated transfer reduction of freebase 6 in the prior process (FIG. 1), the reduction of 6a to 7 (in FIG. 2) is advantageously a scalable and robust catalytic hydrogenation that not only circumvents the use of super-stoichiometric amounts of zinc but also reduces the risk of forming genotoxic impurities, principally chloromethane, but also compounds containing nitroso, diazo, or azo-oxide functions, in quantities that can persist as residual unreacted trace quantities in the product. Use of Zinc also leads to undesirable impurities that include deschloro and des-fluoro forms of the reduced product.

After experimenting with various combinations of catalysts and solvents in the reduction of 6 to provide 3 (as shown in the generalized scheme of FIG. 7), it was discovered that platinum-based catalysts gave superior results in terms of chemoselectivity and reactivity, whereas all tested palladium-based catalysts produced significant amounts of the hydro-dechlorination (des-chloro) side product 10 and in some cases des-fluoro impurities (not shown). Either or both of these side products can persist as impurities in the intermediate 3.

To specifically test how the platinum-based catalysts performed with the corresponding hydrochloride salt 6a instead of freebase 6, further studies at lower catalyst loadings identified 1% Pt-2% V/C (wet loading) as an optimal catalyst. Vanadium-doping has been shown to considerably improve the safety, selectivity, and performance of Pt-catalyzed hydrogenations. (See, e.g., Loos, P.; Alex, H.; Hassfeld, J.; Lovis, K.; Platzek, J.; Steinfeldt, N.; Hubner, S., Selective Hydrogenation of Halogenated Nitroaromatics to Haloanilines in Batch and Flow, Org. Process. Res. Dev., (2015), 20, 452-464; D. Formetti, F. Ferretti, F. K. Scharnagl, M. Beller, Chem. Rev. (2019), 119, 2611-2680; and Baumeister, P.; Blaser, H.-U.; Studer, M., Strong reduction of hydroxylamine accumulation in the catalytic hydrogenation of nitroarenes by vanadium promoters, Catal. Lett., (1997), 49, 219-222.) Addition of a base is effective to quench formation of the des-Cl byproduct 10; without base, 10 can be present in as much as 1-2 wt. % whereas with a base, this amount can be reduced to <0.1 A %. Whereas platinum, doped with vanadium, exists as a preferred and effective catalyst for this nitro-reduction step, one skilled in the art would appreciate that other catalyst systems, subject to any applicable optimization, may have comparable efficacy.

Accordingly, in one embodiment, the conditions facilitated a one-step protocol to achieve nitro group reduction of 6. This proceeded via simultaneous in-situ freebasing of 6a with a base such as aqueous ammonia solution at a mol. equiv. of 0.1-5, preferably 1.5-3 eq., and more preferably 2.5 eq., and hydrogenation of the freebase at a hydrogen pressure of 0.1-100 bar, preferably 1-10 bar, and most preferably 2.8-3.0 bar. In this step, a catalyst loading (dry catalyst) of 0.2-5 wt. % can be deployed (FIG. 8); preferably 0.4-1 wt. %, and still more preferably 0.5 wt. %. Suitable organic solvents for this step include THF and 2-MeTHF, and the reaction temperature is in the range 30-80° C., preferably 50° C. This one-step freebasing/hydrogenation protocol delivered the desired product 3 with >99.5 A % in 88-93% isolated yield after crystallization from 2-MeTHF/n-heptane.

In another embodiment, optimized for scaled-up conditions, it was established that even small amounts of residual aniline hydrochloride starting material 5 in the starting sample of 6a resulted in stalling of the hydrogenation reaction and irreproducible yields of 7. Consequently, a two-step protocol involving freebasing with ammonium hydroxide followed by catalytic hydrogenation was found to be more reliable and reproducible for large scale production, as trace amounts of starting material 5 were purged during the freebasing step (FIG. 9). As further described in Example 12 herein, such a two-step process afforded 94% yield of penultimate intermediate 7 on a 21 kg scale in >99.9 A % HPLC purity after crystallization from 2-MeTHF/n- heptane. The 2-MeTHF solvent is additionally useful because it avoids formation of the genotoxic impurity, methyl chloride.

Amide Coupling

The penultimate synthetic step of the manufacturing route (FIG. 2) is the amide coupling of isoquinoline intermediate 7 with thienopyrimidine 2 to generate crude quantities of 1b. A prior scheme (FIG. 1) involved the coupling of 7 with pyrimidone 3 to produce the chloropyrimidine intermediate 8, which is sensitive to subsequent hydrolysis, and which requires a further step to produce 1b. The amide coupling of FIG. 1 also resulted in the formation of several impurities. By using thienopyrimidine 2 as the starting material in place of 3 (as in FIG. 2), the instability of 8 is addressed, and 1b is formed directly.

Another prior process utilized a coupling of 2 and 7 to create the bis-HCl salt of 1, but had at least the following drawbacks: the low nucleophilicity of the amine coupling partner 2, and the low solubility of the bis HCl salt. Considering the known shortcomings of the bis-hydrochloride salt 1a as a salt that could be viably purified, the product is instead isolated as its bis-mesylate salt 2MSA (1b). By using different reagents (such as TCFH), and reaction conditions (such as N-methyl pyrrolidine as the solvent), as well as introducing methanesulfonic acid after the coupling, the resulting process step is highly robust, scalable and produces fewer impurities than those previously disclosed. An isolation protocol for this step is also preferred, on which a subsequent recrystallization could be based, as further described herein.

Figure 10A:
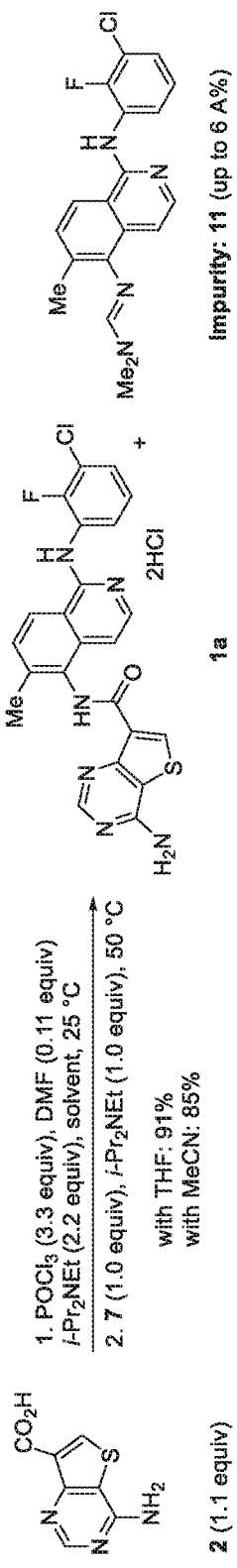
FIG. 10A: First-generation amide coupling with thienopyrimidine 2.

To understand the influence of the reaction conditions on amide coupling, isoquinoline 7 and thienopyrimidine 2 were subjected to the amide coupling conditions of the prior process (FIG. 10A). This reaction afforded the bis-HCl salt of 1 in yields of 85 and 91%, in respectively MeCN and THF. Nonetheless, significant amounts of the amidine side product 11 were formed by reaction with DMF (the catalyst that produces the Vilsmeier reagent in situ) regardless of the solvent. Attempts to lower the DMF loadings lead to a pronounced drop in reactivity of 7. Owing to this detrimental side reaction and the drawbacks of $POCl_3$ (its safety, and practical difficulties such as the fact that it is difficult to quench and that multiple basic washes with $Et_3N$ are required), other amide coupling reagents were explored. This particular coupling reaction is very sensitive to the coupling reagent. For example, employing the well-known 1,1'-carbonyldiimidazole (CDI) as the mediator afforded no desired product, while the use of propanephosphonic acid anhydride (T3P) resulted in low yields and undesired wall cake formation. Overall, N,N,N',N'-tetramethylchloroformamidinium hexafluorophosphate (TCFH) was found to be the most optimal amide coupling reagent for this process step (Table 1). (See, e.g., Beutner, G. L.; Young, I. S.; Davies, M. L.; Hickey, M. R.; Park, H.; Stevens, J. M.; Ye, Q., TCFH-NMI: Direct Access to N-Acyl Imidazoliums for Challenging Amide Bond Formations, *Org. Lett.*, (2018), 20, 4218-4222.)

Figure 10B:
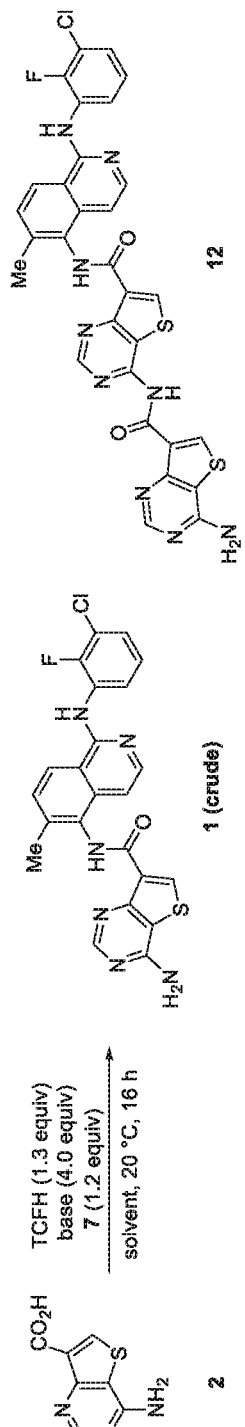
FIG. 10B: Optimization of the amide coupling step.
Figure 10C:
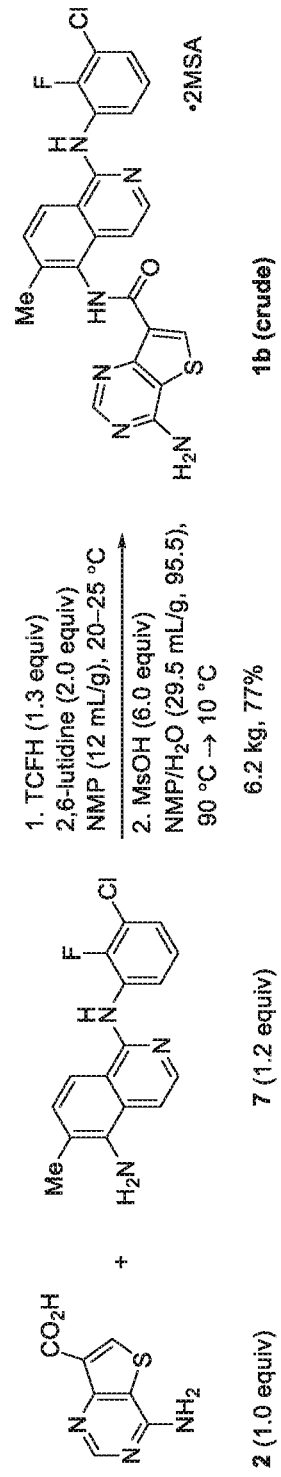
FIG. 10C: Amide coupling and isolation process on a multikilogram scale.

Preliminary experiments with TCFH showed that the solvent MeCN used in the prior process (see FIG. 1) led to the formation of a thick slurry, which significantly extended the subsequent filtration required to isolate 1a. A preliminary solvent screening of strongly polar aprotic solvents that are not as reactive as DMSO revealed excellent performances of both N-ethylpyrrolidone (NEP) and N-methylpyrrolidone (NMP) for achieving both optimal reactivity and homogeneity of the reaction mixture. However, the dimeric impurity 12 was now detected (up to 1.6 A %) with minimal purging success, when using isoquinoline 7 as the limiting reagent (FIG. 10B). With thienopyrimidine 2 as the limiting reagent instead, and N-methylimidazole (NMI) as the base, the formation of impurity 11 was completely suppressed but a lower conversion was observed (Table 1, line 1). Among different bases, 2,6-lutidine, which is less nucleophilic than pyridine, proved to be optimal in NEP and NMP without impurity formation and good conversions (Table 1, entries 3 and 4), as shown in FIG. 10C. The combination of TCFH and 2,6-lutidine is both optimal and would not typically be chosen by those skilled in the art.

Use of solvent such as NEP or NMP is also important; the compounds in this step are poorly soluble in most widely used solvents, thereby limiting the choices available. Several acceptable solvents include: NMP, acetonitrile, THF and MeTHF, of which preferred solvents are NMP and THF.

For the purpose of generating crystalline 1b product in crude form, a HTE solubility screen revealed a combination of NMP/water as an effective solvent system for crystallization. More detailed solubility studies of 1b in variable NMP/water mixtures at 25-80° C. revealed that a cooling crystallization with a constant volume of 5 v % water in NMP would be ideal for achieving high recovery yields and good impurity purging. After completion of the reaction, a filtration step was implemented to remove any insoluble residues, such as lutidine salts, prior to the crystallization.

With these optimized conditions, the amide coupling/isolation step was successfully demonstrated on large scale to afford 6.2 kg of crude 1b in 77% yield and 99.6 A % HPLC purity. Notably, residues and by-products of the amide coupling step, such as chloride, hexafluorophosphate, and 1,1,3,3-tetramethylurea were efficiently purged.

TABLE 1

| entry[a] | solvent | base | 1b (A %)[b] | 12 (A %)[c] | 2 (A %)[c] |
|---|---|---|---|---|---|
| 1 | NEP | NMI | 70.3 | — | 0.9 |
| 2 | NEP | pyridine | 83.3 | 0.7 | — |
| 3 | NEP | 2,6-lutidine | 79.5 | — | — |
| 4 | NMP | 2,6-lutidine | 80.0 | — | — |

[a]Conditions: 2 (0.5 mmol, 1.0 equiv), 3 (1.2 equiv), TCFH (1.3 equiv), base (4.0 equiv.), solvent (14.0 mL/g), 20° C., 16-20 h.
[b]Area percent of 1 relative to starting material 3 by HPLC analysis.
[c]Area percent of 12 or 2 relative to product 1 by HPLC analysis.

A further optimization of the amide coupling step involved isolating a THF solvate of 1, denoted 1 (THF) prior to bis-mesylate formation. The THF solvate has much improved filterability compared to that of the free base. When proceeding in this way, FIG. 10D, the reaction can be quenched with any one of: water, water in i-PrOH, 5% w/w $NH_4OH$, 25% w/w aq. $NH_4OH$, the last two of these being preferred. Pure 1b can be obtained from the THF solvate (also referred to as an adduct) of 1 by the process shown in FIG. 10E in which the solvate is washed with MsOH.

Recrystallization

When working with the crude form of 1b, obtained from the process of FIG. 10C, the main goals of developing a recrystallization were to produce the API with excellent purity, good recovery yields and with good control over its desired physical properties. In particular, it was beneficial to be able to control a crystallization step in order to avoid the multiple slurry purifications that were needed in the method of FIG. 1 to remove impurities from the prior amide coupling step. Nevertheless, obtaining a workable recrystallization protocol for 1b requires overcoming a number of obstacles.

The bis-mesylate salt of 1 is challenging to work with because it is largely insoluble in many solvents and tends to form a gel or a paste. It would be understood by those skilled in the art that crystalline seeds of the material can be obtained, however, by subjecting the material, such as the crude material from the prior amide coupling step, to successive Ostwald ripening cycles.

An initial solubility screen revealed the exceptionally low solubility of 1b in most organic solvents. Notably, DMSO proved to be the only viable solvent in which 1b had a sufficient solubility for experimental optimization. This is notwithstanding the previously established solubility of 1b in NMP; that solvent should not be used due to its toxicity and the allowed limit of ~500 ppm in the final pharmaceutical product. The limit for NMP is considerably lower than the 5,000 ppm permitted for DMSO. One of the reasons for relying on the recrystallization step is to remove an excess of NMP from the final product.

Additionally, it is important to optimize the recrystallization in a manner that minimizes supersaturation and spontaneous nucleation, both of which are forms of uncontrolled crystallization that occur at high concentrations of a solute. These processes are undesirable not just because they are hard to control but because they tend to result in very small particles, which themselves present filtration challenges similar to those found for the bis-HCl salt 1a. Such considerations suggest use of an anti-solvent driven crystallization.

The selection of an appropriate anti-solvent is based at least in part on good miscibility with the other solvent(s) being used, low solubility of the solid form (to give desired form), and the ability to effectively remove impurities. To ensure the best control and purge of inorganic impurities in the crude product, water was selected as the anti-solvent. To this end, a more detailed solubility study of the crude material in DMSO/water mixtures at 10, 70, 75 and 80° C. indicated a steep dependence of the solubility of 1b on water content, with temperature having a smaller impact on recovery yield.

An exemplary anti-solvent recrystallization of crude 1b was test, as follows. The crude material was first heated until fully dissolved in DMSO (5.78 g/g API) at 75° C. This was followed by addition of water (22 wt. %) to bring the system into the metastable zone, seeding at the same temperature, aging for 2 h, and cooling to 20° C. with a rate of 0.2 K/min. This protocol, however, led to the unexpected formation of the mono-mesylate form with a moderate yield of 61% accompanied by high mother liquor losses of up to 35%. The mono-mesylate, disadvantageously, has high solubility in this solvent system (meaning that it is harder to crystallize out of it), and, from other studies, has shown poor crystallinity. It is also difficult to produce in a manner that reliably avoids full or partial conversion of crude material to the bis mesylate, meaning that it is an end-product whose formation is both hard to control and is unstable, and therefore unsuitable for a pharmaceutical grade formulation.

To avoid the undesired loss of methanesulfonic acid and deliver the desired crystal form of 1b, a revised recrystallization approach was implemented, involving the addition of 2.0 equiv. of methanesulfonic acid to the free base. But even this was not straightforward. Correspondingly, a number of impactful improvements were applied: 1) the seed temperature was increased to 80° C. to minimize the propensity for uncontrolled spontaneous secondary nucleation before the addition of seeds; 2) the initial water content was lowered from 22 to 5 wt. % to decrease the super-saturation at seeding and another portion of water (42 wt. %) was added after 30 min. aging to de-saturate the system; and 3) the end temperature was decreased to 10° C. to boost the recovery yield.

Furthermore, the addition rate of water and the stir rate were both optimized, as these parameters were anticipated to impact the particle size distribution (PSD) and filterability of the API upon scale-up. Exemplary apparatus, materials and conditions for exploring these parameters at 50 g scale include: An OptiMax Advanced Synthesis Workstation (Mettler Toledo) using a 1000 mL two-piece glass reactor equipped with a PTFE cover and an overhead pitch-blade impeller (Alloy-C22, 38 mm diameter, downward) at stir rates 200-600 rpm and water addition rates of 4-30 mL/min. Filtration rate was determined by filtering solids at 10° C. over a medium glass sintered funnel (8.5 cm). The crystallization process initially delivered long needle-shaped crystals after seeding that tended to attrit over time and contributed to extended filtration times.

Figure 11:
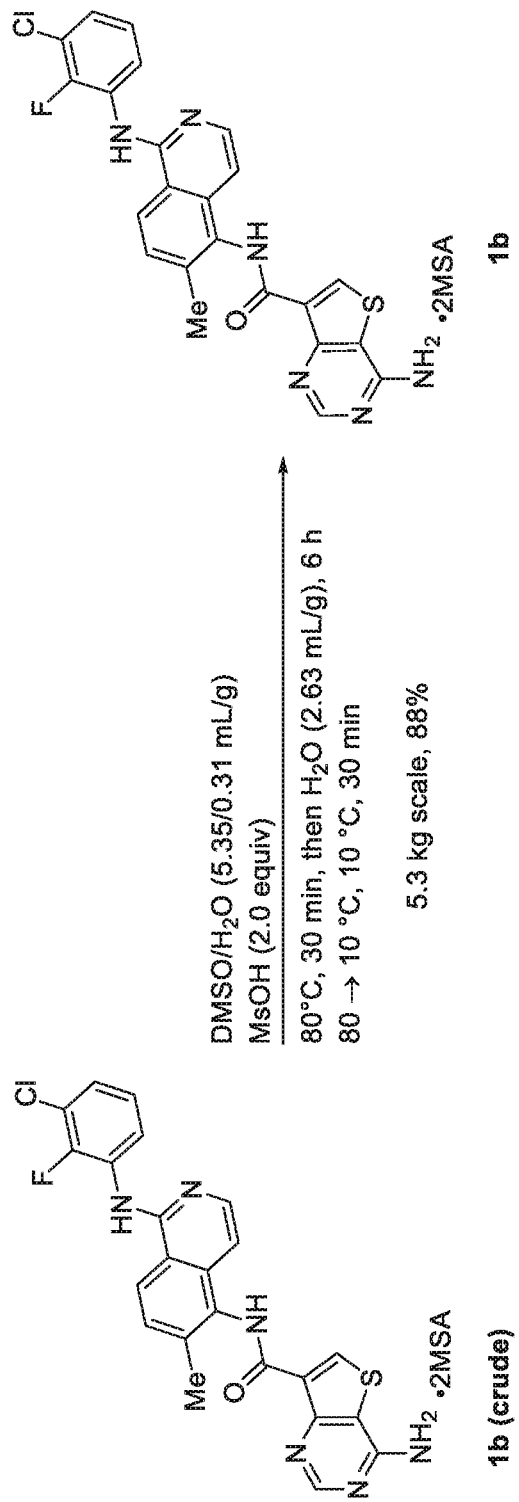
FIG. 11: Recrystallization of 1b.
Like reference symbols in the various drawings indicate like elements.

Subsequently, computational fluid dynamics was applied to model equivalent meso-mixing for manufacture at kilogram scale in order to identify crystallization conditions that provide similar quality results in a larger reactor. (For example, Dynochem calculated equivalent meso-mixing at 8 kg scale with a water addition time of more than 6 h and stir rate of less than 80 rpm compared to the Optimax experiments.) With these optimized reaction conditions, the recrystallization step was performed on a 5.3 kg scale, using DMSO, delivering the final product 1b in 88% yield and 99.8 A % HPLC purity (FIG. 11).

Despite the challenges posed by the poor solubility of 1b in a variety of solvents, it is known that the material can be recrystallized from other solvents, including 2-PrOH/water. In particular, the ternary mixture of iso-propyl alcohol, water, and methanesulfonic acid provides synergistic conditions that lead to formation of larger particles of 1b thereby leading to an improved isolation process via more rapid filtration.

Polymorphs

The bis-mesylate salt has a more manageable range of polymorphic forms than the bis HCl salt. After carrying out many rounds of polymorphic screening, it has been assessed that there are currently only 3 known mesylate polymorphs, of which Form A for the di-mesylate is easily the most stable and offers a well-defined and controllable particle size distribution. There are at least two other crystal forms of the mono-mesylate, that arise from use of different solvents. One came from ethyl-lactate and water, the other from benzyl-alcohol.

The bis-mesylate affords better control over its stoichiometry than the corresponding bis-HCl salt, due principally to the lower volatility of the methylsulfonic acid (relative to HCl). In addition, the bis-mesylate has lower hygroscopicity than the bis-HCl salt, and does not require micronization due to having better control over its particle size distribution (PSD). The fact that the bis mesylate does not require wet milling, and that its particles have good filterability, provides a further benefit to the process of making it.

By contrast, the bis HCl salt has more than 15 polymorphic forms that easily interconvert and which are therefore challenging to control. In particular, the 2HCl "Form A" is a variable hydrate, making equilibration necessary to maintain desired water level. This form also requires jet milling.

Intermediate Compounds

The invention additionally comprises intermediate compounds, as follows:

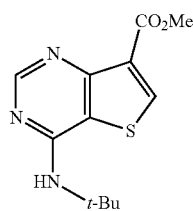

As described elsewhere herein, the invention further comprises methods of synthesis of such compounds.

EXAMPLES

The various examples describe steps in a representative synthesis of 1b. FIG. 2 shows the synthetic pathway in overview. Other steps to prepare various starting materials are described elsewhere herein.

All reactions were performed under an ambient atmosphere of nitrogen unless otherwise stated. Commercially available reagents and solvents were used as received unless otherwise specified. The following catalysts were employed for the nitro-group reduction of compound 6a: Pt/C Evonik F1015RE, Pt(S)/C Evonik F 1082 QHA, Pt/V/C Evonik CF 1082 BV.

Analytical HPLC analyses were performed with an Agilent 1260 Infinity Series HPLC instrument.

$^1$H NMR spectra were recorded on a Bruker 400 (at 400 MHz) and are reported relative to the residual solvent peak (δ=7.26 ppm for CDCl$_3$). Data for $^1$H NMR spectra are reported as follows: chemical shift (δ ppm), multiplicity, coupling constant (Hz), and integration.

$^{13}$C NMR spectra were recorded on a Bruker 400 (at 101 MHz) and are reported relative the residual solvent peak (δ 77.0 ppm for CDCl$_3$). Data for $^{13}$C NMR spectra are reported in terms of chemical shift (δ ppm).

$^{19}$F NMR spectra were recorded on a Bruker 400 (at 376 MHz) and are reported in terms of chemical shift (δ ppm).

HRMS data were collected on an Agilent 6530C qTOF equipped with an ESI source in positive ionization mode.

Melting points were measured on a Büchi Melting Point B-540 apparatus or by differential scanning calorimetry.

Example 1: Thieno[3,2-d]pyrimidin-4(3H)-one (22

A reactor was charged with 20 (76.4 kg, 486 mol, 1.00 equiv.), formamidine acetate 21 (111 kg, 1070 mol. 2.2 equiv.), 2-methoxyethanol (608 kg) and the contents were heated to 110-125° C. for 10 h. After completion of the reaction (20=0.03 A % (spec.≤0.5 A %)), the mixture was cooled to 20-25° C. and the solvent reduced in vacuo to 3-7 V at ≤90° C. batch temperature. After cooling to 15-30° C., water (252 kg) was slowly added and the contents were stirred for 7 h. The contents were centrifuged, the wet cake washed with water (20.0 kg), and the cake then dried under reduced pressure at 45° C. for 21 h to afford 22 (63.2 kg, 85%) as an off-white solid.

HPLC: >99.9 A %; 100 wt. % assay. M.p.: 220-222° C. (DSC). $^1$H NMR (400 MHz, DMSO-d$_6$) δ 12.45 (s, 1H), 8.19 (d, J=5.3 Hz, 1H), 8.16 (s, 1H), 7.41 (d, J=5.3 Hz, 1H). $^{13}$C NMR (101 MHz, DMSO-d$_6$) δ 158.2, 157.9, 147.0, 135.4, 125.7, 123.5. HRMS (ESI+) calculated for C$_6$H$_5$N$_2$OS [M+H]$^+$ m/z 153.0117, found 153.0117.

Example 2: 7-Bromothieno[3,2-d]pyrimidin-4(3H)-one (23

To a first reactor (R1) were added 22 (63.1 kg, 415 mol, 1.00 equiv., 100 w %), anhydrous sodium acetate (68.0 kg, 830 mol., 2.00 equiv.), acetic acid (592 kg), and the contents were heated to 55-65° C. To a second reactor (R2) were added bromine (267 kg, 1660 mol, 4.00 equiv) and acetic acid (63.1 kg). The mixture in R2 was slowly added to R1 and the contents were heated for 12 h at 55-65° C. After completion of the reaction (22=1.9 A %, HPLC), the reaction mixture was cooled to 20-30° C., an aqueous solution of sodium sulfite (782 kg, 20.0 wt. %) was charged and the mixture was stirred for 3 h at 20-30° C. Water (126 kg) was then added portion-wise to R1 and the contents stirred for 2 h. After centrifuging, the wet cake was rinsed three times with water (3×16.0 kg). The wet cake was then slurried in R1 with water (662 kg, 10.5×) for 3 h at 20-30° C., centrifuged, and washed five times with water (16.0 kg, 22.0 kg, 14.0 kg, 24.0 kg, 96.0 kg), followed by methanol (24.0 kg). R1 was then rinsed with water (94.0 kg) and the rinse transferred to the wet cake. After centrifuging, the wet cake was sequentially rinsed with water (18.0 kg) and methanol (22.0 kg). Drying at 45° C. for 21 h under vacuum delivered the product 23 (80.7 kg, 75%) as an off-white solid.

HPLC: 97.0 A %; 88.3 wt % assay. M.p.: 336-338° C. (DSC). $^1$H NMR (400 MHz, DMSO-d$_6$) δ 12.76 (s, 1H), 8.39 (s, 1H), 8.27 (s, 1H). $^{13}$C NMR (101 MHz, DMSO-d$_6$) δ 157.3, 154.7, 148.1, 132.5, 123.2, 109.1. HRMS (ESI+) calculated for C$_6$H$_4$BrN$_2$OS [M+H]$^+$ m/z 230.9222, found 230.9225.

Example 3: 7-Bromo-4-chlorothieno[3,2-d]pyrimidine (24

A reactor was charged with 23 (74.6 kg, 311 mol, 1.00 equiv, 96.4 wt %), toluene (638 kg), followed by hydrobromic acid in acetic acid (10.8 kg, 44.1 mol, 0.14 equiv, 33.0 wt %). Another portion of toluene (6.00 kg) was charged and the contents were stirred for 30 min. POCl$_3$ (102 kg, 665 mol, 2.14 equiv.), toluene (10.0 kg) and Et$_3$N (42.0 kg, 415 mol, 1.33 equiv) were then added. The contents were heated at 80-95° C. for 3-6 h. After completion of the reaction (23=0.10 A % HPLC), the reaction temperature was adjusted to 20-40° C. and the solution concentrated to 2-3 V (148-222 L) at ≤40° C. batch temperature. Toluene (324 kg) was charged and concentrated to 2-3 V, followed by CH$_3$CN (302 kg), and concentration to 2-3 V at ≤40° C. batch temperature. This step was repeated with CH3CN (273 kg) until the residual toluene was less than 2 wt %. Water (1480 kg) was added slowly at 0-10° C., followed by sodium bicarbonate (111 kg) to reach pH=7-8. The contents were then stirred at 15-25° C. for 30 min, centrifuged, and the wet cake was rinsed with water (2×32.0 kg, then 30.0 kg). Drying in vacuo at 45° C. for 21 h afforded the product 24 (76.1 kg, 96%) as an off-white solid. HPLC: 99.5 A %; 98.0 wt % assay. M.p.: 179-181° C. (DSC). 1H NMR (400 MHz, DMSO-d6) δ 9.17 (s, 1H), 8.80 (s, 1H). $^{13}$C NMR (101 MHz, DMSO-d6) δ 158.5, 155.5, 154.7, 136.8, 129.8, 109.3. HRMS (ESI+) calculated for C6H3BrClN2S [M+H]+ m/z 248.8883, found 248.8874.

Example 4: 7-Bromo-N-(tert-butyl)thieno[3,2-d]pyrimidin-4-amine (25

To a reactor were added 24 (85.1 kg, 336 mol, 1.00 equiv, 98.3 wt %), isopropanol (611 kg), tert-butylamine (99.5 kg, 1360 mol, 4.04 equiv), followed by isopropanol (48.0 kg). The contents were heated to 95-105° C. for 20 h at reduced pressure (1-4 bar). After completion of the reaction (24=n.d.), the temperature was adjusted to 20-30° C., isopropanol (160 kg) was added and the mixture heated to 95-105° C. for 2 h at <4 bar. Another portion of isopropanol (238 kg) was charged and the contents were reduced to 2-3 V (170-255 L) at ≤50° C. batch temperature. The mixture was then cooled down to 20-30° C., and two portions of water (224 kg, 645 kg) were charged. After centrifuging, the wet cake was washed three times with water (115 kg, 112 kg, 125 kg) and dried at 40-50° C. under reduced pressure for 24 h. The drying process was repeated once until 0.2 wt % water content was reached. The product 25 (92.3 kg, 96%) was obtained as an off-white solid. HPLC: 99.0 A %; 100 wt % assay. M.p.: 199-200° C. (DSC). $^1$H NMR (400 MHz, DMSO-$d_6$) δ 8.53 (s, 1H), 8.28 (s, 1H), 7.36 (s, 1H), 1.52 (s, 9H). $^{13}$C NMR (101 MHz, DMSO-d6) δ 157.2, 155.6, 155.0, 130.0, 115.3, 108.9, 52.9, 29.1. HRMS (ESI+) calculated for C10H13BrN3S [M+H]+ m/z 286.0008, found 285.9995.

Example 5: Methyl 4-(tert-butylamino)thieno[3,2-d]pyrimidine-7-carboxylate (26

A first reactor R1 was charged with 25 (110 kg, 386 mol, 1.00 equiv, 100 wt. %) and methanol (1659 kg) and the mixture was filtered at 20-30° C. for 12 h. The filter was washed with methanol (80.0 kg) and the washes were added to R1. Pd(OAc)2 (1.29 kg, 5.79 mol, 1.50 mol %), (R)-BINAP (5.35 kg, 9.65 mol, 2.25 mol %), triethylamine (133 kg), and methanol (14.0 kg) were then added. The contents were reacted under CO atmosphere (8-13 bar) at 80-90° C. for 26 h until completion of the reaction (25=n.d.). The mixture was transferred into a second reactor R2 together with the $CH_2Cl_2$ (198 kg) rinses of R1. The reaction mixture of an independent run with 25 (11.0 kg, 32.1 mol, 83.6 wt %) were combined with the contents of R1 and concentrated to 2-3 V (220-330 L) under reduced pressure at ≤50° C. $CH_2Cl_2$ (5536 kg) was added at 20-30° C. and the contents of R2 were stirred for 2 h. An aqueous solution of imidazole (485 kg, 10.0 wt %) was added, the mixture stirred for 3 h at 10-30° C., and the phases were separated. The combined organic phases were transferred into reactor R3 with $CH_2Cl_2$ (240 kg) rinsed of R2, concentrated to 2-3 V (220-330 L) under reduced pressure at ≤35° C., and then MeCN (150 kg) was added. The mixture was concentrated to 2-3 V (220-330 L) under reduced pressure at ≤35° C. and the procedure repeated twice with MeCN (125 kg, 113 kg) until the content of $CH_2Cl_2$ was reduced to 1.0 wt %. R3 was then charged with MeCN (223 kg) and the mixture stirred at 20-30° C. for 2 h. After centrifuging, the wet cake was rinsed twice with MeCN (75.0 kg, 70.0 kg). The wet cake was then transferred back into R3, MeCN (297 kg) was added, and the contents stirred for 2 h at 20-30° C. After centrifuging, the wet cake was rinsed with MeCN (103 kg). Drying at 40-50° C. for 15-20 h afforded 26 (97.2 kg, 83%) as an off-white solid. HPLC: 100 A %; 94.9 wt % assay. Pd=21 ppm (spec.: <50 ppm). M.p.: 242-244° C. (DSC). $^1$H NMR (400 MHz, DMSO-$d_6$) δ 8.84 (s, 1H), 8.54 (s, 1H), 7.29 (s, 1H), 3.84 (s, 3H), 1.52 (s, 9H). $^{13}$C NMR (101 MHz, DMSO) δ 162.3, 157.3, 156.4, 155.0, 141.7, 127.4, 117.0, 52.8, 52.2, 29.1. HRMS (ESI+) calculated for $C_{12}H_{16}N_3O_2S$ [M+H]+ m/z 266.0958, found 266.0942.

Example 6: 4-Aminothieno[3,2-d]pyrimidine-7-carboxylic acid (2

A first reactor R1 was successively charged with 26 (47.8 kg, 171 mol, 1.00 equiv, 94.9 wt %), glacial acetic acid (250 kg), concentrated sulfuric acid (34.4 kg, 351 mol, 2.05 equiv), and glacial acetic acid (13.0 kg). The contents were reacted at 75° C. for 40 h until completion of the reaction (26=1.2 A % HPLC). The mixture was then concentrated to 2-3 V (95-143 L) under reduced pressure at ≤40° C., ethanol (150 kg) was added, and the contents were again concentrated to 2-3 V (95-143 L) under reduced pressure at ≤40° C. (acetic acid <0.1 wt. %). The reactor was then charged with water (948 kg), followed by an aqueous solution of KOH (694 kg, 10.0 wt %) at ≤30° C. until reaching pH=13 (pH=12-14). The contents were transferred into a second reactor R2 and combined with the water (30.0 kg) rinses of R1. The mixture was heated at 50° C. for 2 h and then cooled down to 15-35° C. Glacial acetic acid (30.4 kg) was charged into R2 until pH=5.5 (pH=4.5-5.5) was reached, and the contents were then stirred for 1-2 h at 15-35° C. After completion of the reaction (2=95.4 A % HPLC) and centrifuging, the wet cake was rinsed with water (140 kg) and transferred back into R2. Acetone (364 kg) was then charged into R2 and the mixture heated at 25-60° C. for 6 h. After centrifuging, the wet cake was rinsed with water (90.0 kg), and then dried at 25° C. for 3 h at reduced pressure. After drying at 50-55° C. for 126 h (KF=1.2%), the product 2 (32.0 kg, 96%) was afforded as an off-white solid. HPLC: 99.7 A %; 100 wt % assay. M.p.: 279-281° C. (DSC). $^1$H NMR (400 MHz, DMSO-$d_6$) δ 8.92 (s, 1H), 8.51 (s, 1H), 7.94 (s, 2H). $^{13}$C NMR (101 MHz, DMSO-$d_6$) δ 162.2, 159.2, 156.3, 155.2, 142.7, 126.8, 115.0. HRMS (ESI+) calculated for $C_7H_6N_3O_2S$ [M+H]+ m/z 196.0175, found 196.0163.

Example 7: 6-Methyl-5-nitroisoquinoline (42

Reactor R1 was charged with 5-nitroisoquinoline (40) (80.1 kg, 460 mmol, 1.00 equiv), THF (438 kg), the mixture was cooled to 20-30° C., and stirred for 2 h. Ethyl 2-chloroacetate (41) (85.0 kg, 694 mmol, 1.50 equiv) and THF (40.0 kg) were then added into R1 and stirred at 20-30° C. for 2 h. The solution in R1 was transferred into drums; R1 was charged with THF (432 kg) and KOt-Bu (155 kg, 1382 mol, 3.00 equiv) and the contents were cooled to −15-0° C. The solution of the starting materials in THF was then slowly added into R1 at −15-0° C., the drums were rinsed with THF (36.0 kg), the rinse combined with the contents of R1 and stirred at −15-0° C. for 10.5 h. Water (810 kg) was charged into R1 at −15-0° C. and the contents were stirred at 0° C. for 2 h, followed by addition of conc. HCl (254 kg, 36.0 wt %) into R1 below 30° C. until pH=1. The contents of R1 were heated to 85-95° C., concentrated to 1250 L (13-15×) at ambient pressure, and stirred at 85-95° C. for 24 h. Water (1132 kg) was added into R1 at 20-30° C., followed by aq. NaOH solution (250 kg, 30.0 wt %) until pH=4-5. After filtration, the wet cake and acetone (1,253 kg) were charged back into R1, and the contents were stirred for 2 h at 20-30° C. After filtration over diatomite (20.0 kg) and washing with acetone (400 kg), the filtrate was transferred back into R1 and cycled over a CUNO filter for 16 h. The solution in R1 was concentrated to 450 L under reduced pressure at <50° C., and water (810 kg) was slowly added into R1 at 40-50° C. R1 was then cooled to 20-30° C. over 3 h and stirred for 4 h. After filtration and water rinses (521 kg), wet 42 (80.0 kg, 74%) was obtained as a brown solid. HPLC: 99.2 A %; 79.5 wt % assay. M.p.: 134-136° C. (DSC). $^1$H NMR (400 MHz, CDCl$_3$) δ 9.30 (d, J=1.0 Hz, 1H), 8.66 (d, J=6.1 Hz, 1H), 8.05 (d, J=8.4 Hz, 1H), 7.60 (dd, J=6.1, 1.0 Hz, 1H), 7.54 (d, J=8.4 Hz, 1H), 2.60 (s, 3H). $^{13}$C NMR (101 MHz, CDCl$_3$) δ 152.2, 146.2, 145.6, 133.4, 130.4, 129.9, 127.9, 127.2, 114.2, 18.6. HRMS (ESI+) calculated for $C_{10}H_9N_2O_2$ [M+H]+ m/z 189.0659, found 189.0654.

Example 8: 6-Methyl-5-nitroisoquinoline-N-oxide (43

OXONE® (390 kg, 634 mol, 0.76 equiv.) and water (1900 kg) were charged into R1, the contents stirred at 15-25° C. until full dissolution and then transferred into drums. Water (786 kg) was charged into R1, cooled to 0-20° C., followed by slow addition of concentrated $H_2SO_4$ (174 kg, 1776 mol, 2.10 equiv.) at 0-20° C. The contents of R1 were then stirred at 0-20° C. for 1 h, and thereafter transferred into drums. Compound 42 (158 kg (net amount), 840 mol, 1.00 equiv) and water (962 kg) were added into R1, heated to 50-60° C., and the oxone/water solution was then slowly charged into R1 at 50-60° C. The contents were stirred at 50-60° C. for 15 h, the temperature adjusted to 70-80° C., followed by addition of the aq. $H_2SO_4$ solution at 70-80° C. After stirring at 70-80° C. for 1 h, the mixture was cooled to 15-25° C. over 4 h, and then stirred for 2 h. After filtration and water rinses (650 kg), the wet product 43 was isolated (193 kg, 76%) as a yellow solid. HPLC: 96.0 A %; 67.3 wt % assay. M.p.: 194-196° C. (DSC). $^1$H NMR (400 MHz, DMSO-$d_6$) δ 9.09 (d, J=1.8 Hz, 1H), 8.26 (dd, J=7.5, 1.8 Hz, 1H), 8.05 (d, J=8.6 Hz, 1H), 7.73 (d, J=8.6 Hz, 1H), 7.70 (d, J=7.5 Hz, 1H), 2.47 (s, 3H). $^{13}$C NMR (101 MHz, DMSO-d6) δ 146.2, 139.9, 135.7, 132.9, 131.5, 129.2, 128.4, 119.5, 118.8, 18.1. HRMS (ESI+) calculated for $C_{10}H_9N_2O_3$ [M+H]+ m/z 205.0608, found 205.0603.

Example 9: 1-Chloro-6-methyl-5-nitroisoquinoline (4

Compound 43 (50.3 kg (net amount), 247 mol, 1.00 equiv) and $CH_3CN$ (785 kg) were charged into reactor R1 and the contents concentrated at <45° C. under reduced pressure 150 L (2-3×). This process was once repeated with $CH_3CN$ (791 kg) until KF=0.20%. $CH_3CN$ was then swapped with $CH_2Cl_2$ (2,472 kg) and the mixture was then concentrated to around 1,000 L (~20 V). LiCl (10.0 kg, 236 mol, 0.96 equiv) and DMF (2.00 kg, 27.3 mol, 11.1 mol %) were charged into R1, followed by $POCl_3$ (76.6 kg, 500 mol, 2.02 equiv) at 35-45° C. and the mixture of R1 was stirred at 35-45° C. for 17 h until completion of the reaction (43=0.2 A % HPLC). Water (496 kg) was then added into R1 below 30° C. and the mixture was stirred at 20-30° C. for 1 h. After separation, the organic phase was added back to R1, water (500 kg) and $NaHCO_3$ (30.0 kg) were added into R1 below 30° C. until pH=7-8. The mixture was stirred at 20-30° C. for 1 h and the phases separated. The organic phase was added to reactor R2, cycled over a CUNO filter for 16 h, concentrated at <45° C. under reduced pressure to 200 L (3-5 V), followed by swapping $CH_2Cl_2$ with THF (1200 kg). Another portion of THF (580 kg) was charged into R2, the contents heated at 40-50° C. for 3 h; water (504 kg) was added into R2 at 40-50° C. over 3 h and the contents were stirred at 40-50° C. for 1 h. R2 was cooled to 20-30° C. over 2 h, stirred for 4 h and the wet cake was isolated after centrifugation and water rinses (172 kg). MEK (477 kg) was added to the wet cake, the solution was distilled at <40° C. under vacuum to around 100 L (2 V). n-Heptane (682 kg) was then added to R2 within 3 h at 30-40° C., stirred for 1.5 h, and then for 4 h at 20-30° C. The wet cake was isolated after centrifugation and rinsing with n-heptane (102 kg), followed by drying at 30-40° C. jacket temperature for 3 h, then at 40-50° C. for 24 h. Product 4 was afforded as an off-white solid (29.3 kg, 53%). HPLC: 99.8 A %; 99.4 wt % assay. M.p.: 176-178° C. (DSC). 1H NMR (400 MHz, $CDCl_3$) δ 8.41 (d, J=8.7 Hz, 1H), 8.38 (d, J=6.0 Hz, 1H), 7.60 (d, J=8.7 Hz, 1H), 7.50 (d, J=6.0 Hz, 1H), 2.58 (s, 3H). $^{13}$C NMR (101 MHz, CDCl3) δ 151.9, 146.6, 144.0, 134.1, 131.0, 129.7, 129.0, 125.5, 114.3, 18.4. HRMS (ESI+) calculated for $C_{10}H_8ClN_2O_2$ [M+H]+ m/z 223.0269, found 223.0269.

Example 10: 3-Chloro-2-fluoroaniline hydrochloride (5a

To a reactor were added KF (190 kg, 3270 mol, 2.09 equiv), 18-Crown-6 (830 kg, 3143 mol, 2.01 equiv), DMA (1650 kg), and toluene (1000 kg). The mixture solution was heated to 140-145° C. over 5 h, stirred for 2 h, and concentrated at 140-145° C. until KF<0.02%). 1,2-dichloro-3-nitrobenzene 50 (298 kg, 1561 mol, 1.00 equiv) was added to the mixture at 140-145° C. and the contents were stirred for 19.5 h until completion of the reaction (50=0.10 A % HPLC). The reaction mixture was then cooled down to 20-40° C. over 5 h. After addition of Raney-Ni (5.30 kg, 1.8 wt %), the mixture was reacted for 17 h at 70-80° C. under a hydrogen pressure of 12-15 bar until completion of the reaction (freebase 5=1.70 A % HPLC). The mixture was cooled down to 20-40° C., the catalyst was removed by filtration, and water (580 kg) was added. The solution was then extracted with MTBE (367 kg) and the organic phase was washed with an aq. solution of NaOH (350 kg, 5.0 wt. %). After phase separation and filtration, the filtrate was slowly added into a solution of 7.0 wt % HCl in MTBE/MeOH (100:1, 1000 kg). The solution was stirred at 40-50° C. for 2 h and then at 20-25° C. for 5 h. The wet cake was washed with MTBE (160 kg) and then added into a solution of EtOAc (640 kg) and water (26.0 kg). The suspension was finally stirred for 5 h at 25° C., filtered and washed with EtOAc (170 kg). After drying under vacuum at 40° C. for 24 h, compound 5a was yielded as an off-white solid powder (99.7 kg, 35% over three steps). HPLC: 100 A %; 99.8 wt % assay (freebase 5: 79.8 wt. % freebase). M.p.: 173-175° C. (DSC). $^1$H NMR (400 MHz, $CD_3OD$) δ 7.62 (ddd, J=8.3, 6.8, 1.6 Hz, 1H), 7.50 (ddd, J=8.2, 6.8, 1.6 Hz, 1H), 7.35 (ddd, J=8.3, 8.2, 1.5 Hz, 1H). $^{13}$C NMR (101 MHz, $CD_3OD$) δ 151.8 ($1J_{C-F}$=253 Hz), 130.5 ($3J_{C-F}$=5.9 Hz), 125.7, 123.1, 122.0 ($2J_{C-F}$=15.0 Hz), 121.2. $^{19}$F NMR (376 MHz, $CD_3OD$) δ −129.2. HRMS (ESI+) calculated for $C_6H_6ClFN$ [M+H]+ m/z 146.0167, found 146.0167.

Example 11a: N-(3-chloro-2-fluorophenyl)-6-methyl-5-nitroisoquinolin-1-amine hydrochloride (6a According to the scheme in FIG. 6, to a reactor was added 2-butanone (306 kg), 1-chloro-6-methyl-5-nitroisoquinoline (4) (38.0 kg, 171 mol, 1.00 equiv), and 3-chloro-2-fluoroaniline hydrochloride (5a) (34.2 kg, 188 mol, 1.10 equiv.). The resulting suspension was heated to 78° C. and aged for 21 h until the reaction was complete (4<1.0 A % HPLC). The slurry was cooled to 25° C., transferred to another vessel with 2-butanone (91.8 kg), followed by water (12.0 kg) addition. The slurry was aged for 4 h and then filtered. The reactor was rinsed with 2-butanone (184 kg) and the rinse was used to wash the filter cake in portions before drying under vacuum at 35° C. for 21 h. The filter was discharged to give 6a (55.5 kg, 88% yield) as a light yellow solid. HPLC, MS, and NMR as in Example 11b.

Example 11b: N-(3-chloro-2-fluorophenyl)-6-methyl-5-nitroisoquinolin-1-amine hydrochloride (6a According to the scheme in FIG. 6, a triple mantle reactor was charged at 25° C. with 1-chloro-6-methyl-5-nitro-isoquinoline (20.0 g), 3-chloro-2-fluoro-aniline, hydrochloride (17.99 g, 1.1 eq.) and MIBK (120 g). To the suspension was added $NEt_3$ (6.89 mL, 0.8 eq.). The suspension was then heated to 105° C. until 1-chloro-6-methyl-5-nitro-isoquinoline was almost fully consumed (5 h). The reaction suspension was then cooled to 80° C. and water (60 mL) was added. The yellow suspension was stirred at 80° C. for 2 h and cooled down to 25° C. in at least 3.5 hours and stirred at 25° C. overnight. The suspension was filtered on a paper filter and the wet cake was rinsed sequentially with water (20 g), and MIBK (20 g). The wet solid was dried in a rotary evaporator (50° C., p=10 mbar) to afford 30.22 g of a pale yellow powder (91.4% yield, HPLC purity=99.58 area %). HPLC: 99.9 A %; 99.4% assay. M.p.: 221° C. (DSC). 1H NMR (400 MHz, DMSO-$d_6$) δ 8.98 (d, J=8.7 Hz, 1H), 7.90 (d, J=6.7 Hz, 1H), 7.85 (d, J=8.7 Hz, 1H), 7.59 (d, J=8.1 Hz, 1H), 7.57 (d, J=8.1 Hz, 1H), 7.36 (ddd, J=8.2, 8.1, 1.2 Hz, 1H), 6.98 (dd, J=6.7, 0.8 Hz, 1H), 2.53 (s, 3H). 13C NMR (101 MHz, DMSO-$d_6$) δ 153.3 ($1J_{C-F}$=251 Hz), 152.3, 146.7, 136.8, 135.9, 131.0, 129.5, 129.2, 128.8, 127.8, 126.6 ($3J_{C-F}$=11.4 Hz), 126.2 ($3J_{C-F}$=4.6 Hz), 121.4 ($2J_{C-F}$=16.2 Hz), 117.8, 106.1, 18.0. $^{19}$F NMR (376 MHz, DMSO-$d_6$) δ −120.8. HRMS (ESI+) calculated for $C_{16}H_{12}ClFN_3O_2$ [M+H]+ m/z 332.0602, found 332.0597.

Example 12a: N-(3-chloro-2-fluorophenyl)-6-methylisoquinoline-1,5-diamine (7

In one example, a reactor was charged with 6 (27.1 kg, 73.6 mol, 1.00 equiv.) and 2-MeTHF (186 kg). To the suspension was added an aqueous ammonium hydroxide solution (5.20 kg, 81.0 mol, 1.10 equiv, 26.5 wt. %) at 25° C. The resulting yellow suspension was stirred at 25° C. for 3 h. The contents were transferred to a hydrogenation reactor with a 2-MeTHF (50.0 kg) rinse. The catalyst Pt (1%)/V (2%)/C (0.29 kg, 1.06 wt %) was suspended in 2-MeTHF (30.0 kg) and transferred with a 2-MeTHF (36.5 kg) rinse at 25° C. The temperature was adjusted to 50° C. and the reactor filled with hydrogen to 2.9 bar. After 34 h, the temperature was reduced to 25° C. and the reactor depressurized with nitrogen venting cycles. The reaction contents were filtered to remove the catalyst and ammonium chloride salts, followed by a wash with 2-MeTHF (93.0 kg). The filtrate was concentrated under vacuum below 40° C. to 82.5 L volume. Following temperature adjustment to 50° C., n-heptane (276 kg) was charged over 1.5 h to precipitate the product, followed by aging for 1 h. The temperature was adjusted to 5° C. over 8 h, held for 9 h, followed by cooling to 0° C. Filtration was then conducted in portions and the final cake washed with cold n-heptane (115 kg). The resulting solid was dried under vacuum below 45° C. for 13 h to afford 3 (21.0 kg, 94%) as a white solid. HPLC: >99.9 A %; 99.6% assay. ICP-MS: Pt<5 ppm, V<5 ppm. M.p.: 140° C. (DSC). NMR as in Example 12b.

Example 12b: N-(3-chloro-2-fluorophenyl)-6-methylisoquinoline-1,5-diamine (7

In a second example, a reactor was charged with 2-MeTHF (180 kg) and $NH_3$ (aq., 25%, 2.5 eq., 19.8 kg). To the bi-phasic mixture was charged 6 (50 kg) as a solid at ambient temperature. Additional 2-Me-THF (90 kg) was added and the resulting suspension was stirred for at least 15 min. The suspension was transferred into an autoclave and the reactor was washed with 2-Me-THF (105 kg) and water (29 kg). Then a suspension of Pt (1%)-V (2%)/C (0.66 kg wet weight, 1.345% w/w, corresponds to 0.46% w/w of dry catalyst) in 2-Me-THF (9.8 kg) is added to the reaction mixture. The transfer lines were washed with 2-Me-THF (29.7 kg) and the autoclave was rendered inert with vacuum/hydrogen cycles. The reaction mixture was heated to 50±5° C. and the hydrogen pressure was adjusted to 3.0±0.4 bar $H_2$. The reaction was run for at least 4 h until the hydrogen uptake stopped. Then, the hydrogen valve was closed and the reaction mixture was stirred for at least 1 h. The reaction mixture was cooled to ambient temperature and the hydrogen pressure was released from the autoclave. The remaining hydrogen in the autoclave was replaced by nitrogen venting cycles and the reaction mixture was filtered to remove the catalyst. The autoclave was rinsed and the filter cake washed sequentially with 2-Me-THF (133 kg) and water (143 kg), the phases were allowed to separate and the aqueous layer was drained. Water (79 kg) was added to the organic phase and the mixture was stirred for at least 15 min. Then, the stirrer was stopped, the layers were allowed to separate for 15 min and the aqueous phase was drained. The organic player was concentrated under vacuum to ca. 3.75 V (ca. 190 L). Then the vacuum was stopped, the internal temperature was adjusted to 50° C. and n-heptane (86.4 kg) was added over a period of 30 minutes. The reaction mixture was stirred for at least 30 minutes, whereupon a suspension was formed. Additional n-heptane (425 kg) was added over at least 100 minutes followed by a post addition stirring time of 1 h. Then the suspension was cooled to an internal temperature of 0±5° C. at a cooling rate of 10° C./h. After a post stirring time of at least 2 h, the suspension was filtered via a centrifuge, the filter cake was washed with 138.1 kg n-heptane and the isolated crystals were dried under vacuum (<100 mbar, <50° C.) to yield the title compound 7 as white crystals (36.7 kg, 90% yield, 99.8 A % HPLC purity, 99.6% w/w assay). XRF: Pt<1 ppm, V<1 ppm. $^1$H NMR (400 MHz, DMSO-$d_6$) δ 8.82 (s, 1H), 7.79 (d, J=6.0 Hz, 1H), 7.61-7.59 (m, 2H), 7.43 (d, J=6.0 Hz, 1H), 7.34-7.23 (m, 2H), 7.19 (dd, J=8.1, 8.1 Hz, 1H), 5.49 (s, 2H), 2.27 (s, 3H). 13C NMR (101 MHz, DMSO-$d_6$) δ 153.3 ($1J_{C-F}$=247 Hz), 152.2, 141.5, 138.9, 131.5 ($3J_{C-F}$=11.8 Hz), 129.9, 126.0, 125.5, 125.3 ($2J_{C-F}$=31.5 Hz), 125.0 ($3J_{C-F}$=4.5 Hz), 120.4 ($2J_{C-F}$=16.8 Hz), 119.1, 118.3, 110.6, 108.5, 18.5. $^{19}$F-NMR (376 MHz, DMSO-d6) δ −121.5. HRMS (ESI+) calculated for $C_{16}H_{14}ClFN_3$ [M+H]+ m/z 302.0860, found 302.0855.

Example 13a: 4-amino-N-(1-((3-chloro-2-fluorophenyl)amino)-6-methylisoquinolin-5-yl)thieno[3,2-d]pyrimidine-7-carboxamide, tetrahydrofuran (1:1) (1 (THF In a 4 L triple mantle reactor at 25° C. were added 4-aminothieno[3,2-d]pyrimidine-7-carboxylic acid (130 g), N1-(3-chloro-2-fluoro-phenyl)-6-methyl-isoquinoline-1,5-diamine (221.06 g, 1.1 eq.) and 1.3 L of THF. To this white suspension was added 2,6-lutidine (142.72 g, 2.0 eq.) and THF (65 mL). Then N,N,N',N'-tetramethylchloroformamidinium hexafluorophosphate (TCFH, 224.23 g, 1.2 eq.) was added, and the addition funnel was rinsed with THF (260 mL). The reaction mixture was warmed up to 40° C. Additional THF (400 mL) was added to improve the stirrability of the reaction mixture. The conversion of 4-aminothieno[3,2-d]pyrimidine-7-carboxylic acid was monitored via HPLC. After 6 h, satisfactory conversion was achieved. The reaction mixture was cooled down to 15° C. An aqueous solution of 4% w/w NH4OH (1.82 L) was added over 30 minutes to quench the reaction. The quenched reaction mixture was warmed up to 25° C., and stirred at 25° C. for at least 2 h. The suspension was filtered on a paper filter in 30 minutes. The wet cake was rinsed first with water (650 mL), then with acetone (650 mL). The wet cake was dried in an oven (T=50° C.) under vacuum (p=20 mbar) to afford pale yellow crystals (319.97 g, 87.2% yield, HPLC purity=99.4 area %).

$^1$H NMR (DMSO-$d_6$) δ: 11.56 (s, 1H), 9.24 (br s, 1H), 8.94 (s, 1H), 8.58 (s, 1H), 8.35 (d, J=8.7 Hz, 1H), 7.94 (br s, 2H), 7.89 (d, J=6.0 Hz, 1H), 7.62 (d, J=8.7 Hz, 1H), 7.55 (ddd, J=8.2, 6.9, 1.0 Hz, 1H), 7.36 (ddd, J=8.2, 6.9, 1.0 Hz, 1H), 7.23 (ddd, J=8.2, 0.9 Hz, 1H), 7.17 (d, J=6.0 Hz, 1H), 3.55-3.64 (m, 4H), 2.43 (s, 3H), 1.72-1.80 (m, 4H).

X-ray diffraction patterns of 1 (THF) were recorded at ambient conditions in transmission geometry with a STOE STADI P diffractometer (Cu Kα radiation, primary Ge-monochromator, Mythen 1 K silicon strip detector, angular range 3° to 42° 2Theta, 0.02° 2Theta step size, 20 seconds measurement time per step). The samples were prepared and analyzed without further processing (e.g. grinding or sieving) of the substance.

Measurement and evaluation of the X-ray diffraction data was done using WinXPOW software (STOE & Cie GmbH, Darmstadt, Germany). The unique peaks of the crystalline form is presented in Table 2.

TABLE 2

| Peak position [° 2Theta] | Intensity [%] |
| --- | --- |
| 5.23 | 11 |
| 8.94 | 59 |
| 9.87 | 100 |
| 10.85 | 9 |
| 11.64 | 23 |
| 13.04 | 31 |
| 14.47 | 35 |
| 15.22 | 26 |
| 15.74 | 19 |
| 16.24 | 20 |
| 16.52 | 14 |
| 17.27 | 4 |
| 17.96 | 18 |
| 18.16 | 15 |
| 18.72 | 8 |
| 18.97 | 4 |
| 19.26 | 79 |
| 19.82 | 38 |
| 20.67 | 45 |
| 21.94 | 70 |
| 22.17 | 23 |
| 22.57 | 9 |
| 23.41 | 67 |
| 23.62 | 40 |
| 24.36 | 34 |
| 25.59 | 36 |
| 25.98 | 19 |
| 26.15 | 9 |
| 26.41 | 6 |
| 27.03 | 25 |
| 27.34 | 5 |
| 27.71 | 14 |
| 28.01 | 11 |
| 28.53 | 32 |
| 29.30 | 14 |
| 30.70 | 7 |
| 31.50 | 6 |

TABLE 2-continued

| Peak position [° 2Theta] | Intensity [%] |
| --- | --- |
| 37.14 | 8 |
| 40.35 | 10 |

The 5 most significant peaks are at 8.94, 9.87, 19.26, 21.94, and 23.41 values of 2Theta.

Example 13b: Reaction to form 4-amino-N-(1-((3-chloro-2-fluorophenyl)amino)-6-methylisoquinolin-5-yl)thieno[3,2-d]pyrimidine-7-carboxamide bis-mesylate (1b To reactor R1 was added 2 (2.24 kg, 11.5 mol, 1.00 equiv), 7 (4.19 kg, 13.8 mol, 1.20 equiv) and NMP (28.1 kg). The reaction mixture was stirred for 5 min at 20-25° C. and the reactor was then charged sequentially with 2,6-lutidine (2.54 kg, 23.0 mol, 2.00 equiv) and TCFH (4.26 kg, 15.0 mol, 1.30 equiv.) at 20-30° C. NMP (2.58 kg) was then added and the contents were stirred for 6 h at 20-30° C. until completion of the reaction (2≤1.0 A % HPLC).

Example 13c: Isolation of 4-amino-N-(1-((3-chloro-2-fluorophenyl)amino)-6-methylisoquinolin-5-yl) thieno[3,2-d]pyrimidine-7-carboxamide bis-mesylate (1b Isolation: The resulting suspension was filtered into second reactor R2; first reactor R1 was rinsed with NMP (27.2 kg) and the rinses were combined with the contents of R2. Another portion of NMP (6.42 kg) was added to R1 and filtered into R2. The contents of R2 were heated to 90-95° C. over 1 h, methanesulfonic acid (6.60 kg, 69.0 mol, 6.00 equiv.) was added, followed by water (3.51 kg) over 10 min. The reactor was cooled down to 85° C. and seeds (1b, 39.4 g, 1.75 wt. %) were added. Another portion of NMP (1.47 kg) was used to wash down residual seeds. The contents were aged at 80-85° C. for 3 h, cooled down to 10° C. with a ramp of 0.1 K/min and stirred for another 8 h. After filtration, the reactor was rinsed with acetone (46.0 kg), the rinses used for washing the cake, which was followed by a final wash with acetone (14.9 kg). The contents of the filter dryer were dried under vacuum at 40-50° C. for 20 h when the drying endpoint (KF≤4.0%) was met. The crude product 1b was isolated as a white solid (6.16 kg, 77%, 99.6 A % HPLC).

Example 13d: Recrystallization of 4-amino-N-(1-((3-chloro-2-fluorophenyl)amino)-6-methylisoquinolin-5-yl)thieno[3,2-d]pyrimidine-7-carboxamide bis-mesylate (1b) at Scale To a 100 L reactor was charged crude 1b (6.08 kg, 8.75 mol, 1.00 equiv), and dimethylsulfoxide (28.7 kg). The contents of the reactor were heated to 55° C., and then transferred over a 20 μm PTFE membrane filter into another reactor. The transfer lines were rinsed with dimethylsulfoxide (7.10 kg), and methanesulfonic acid (1.70 kg, 17.5 mol, 2.00 equiv) was added to the reaction mixture, the stirring was set to 76 rpm, and the contents were heated to 85° C. Water (1.89 kg) was added, and the reactor was cooled down to 80° C. when the 1b seeds (61.2 g, 1.0 wt %) were added as solids. Then, another portion of water (16.0 kg) was added dropwise over 6 h via a peristaltic pump and the contents were stirred for 2 h at 80° C. The reactor was cooled to 10°

C. with a ramp of 0.1 K/min. At 10° C. the contents were stirred for 30 min. Afterwards, the contents were vacuum filtered (filtration time: 6 h), the reactor was washed with acetone (35.9 kg) and the rinse filtered over the wet cake. The wet cake was rinsed again with acetone (23.9 kg) and the wet cake was dried in a vacuum at 60° C. for 20 h, when the drying endpoint (KF≤3.0%; acetone, DMSO≤4000 ppm; NMP≤450 ppm) was met. The product (1b) was isolated as a white solid (5.29 kg, 88%). HPLC: 99.8%; 97.3 wt % assay (freebase: 70.0 wt %). M.p.: 305-306° C. (DSC). $^1$H-NMR (400 MHz, DMSO-d$_6$) δ 11.24 (s, 1H), 9.33 (s, 1H), 9.07 (bs, 1H), 8.68 (d, J=8.7 Hz, 1H), 8.66 (s, 1H), 7.94 (d, J=8.7 Hz, 1H), 7.79-7.64 (m, 3H), 7.50-7.43 (m, 1H), 7.41 (d, J=7.0 Hz, 1H), 4.72 (bs, 2H), 2.52 (s, 3H), 2.34 (s, 6H). $^{13}$C-NMR (101 MHz, DMSO-d$_6$) δ 159.5, 158.7, 152.5 (1J$_{C-F}$=249 Hz), 150.8, 150.5, 142.6, 141.5, 134.5, 131.0, 130.6, 129.8, 129.2, 129.2, 127.4, 125.7 (3J$_{C-F}$=4.7 Hz), 124.5, 124.1, 123.6, 120.6 (2J$_{C-F}$=16.0 Hz), 116.5, 114.8, 108.9, 39.1, 18.3. $^{19}$F-NMR (376 MHz, DMSO-d$_6$) δ −121.9. HRMS (ESI) calculated for C$_{23}$H$_{17}$ClFN$_6$OS [M+H]+ m/z 479.0857, found 479.0852.

Example 13e: Obtaining 4-amino-N-(1-((3-chloro-2-fluorophenyl)amino)-6-methylisoquinolin-5-yl) thieno[3,2-d]pyrimidine-7-carboxamide bis-mesylate (1b) from THF Solvate of 1

In a reactor 1 (THF) solvate (40.0 g), was properly mixed with water (320.0 g) and 2-propanol (332.0 g) at 25° C. Methane sulfonic acid (aq. 70%, 24.58 g, 2.45 mol eq.) was added rapidly. Subsequently the suspension was heated to 75° C. The clear solution was polish filtered and the filter was flushed with a mixture of water (15.7 g) and 2-propanol (18.0 g). The clear filtrate was cooled to 65° C. and methane sulfonic acid (aq. 70%, 15.55 g, 1.55 mol eq.) was added. After 10 min. the solution was seeded with 1b (previously obtained by running the bis-mesylate formation process without seeding, so that crystallization occurred spontaneously during the process) (1.47 g, 0.03 eq.) suspended in 2-propanol (5.0 g) and aged for min. 3 h. Subsequently the mixture was cooled down to 20° C. Two heating-/cooling-cycles with the following profile were performed: heating from 20° C. to 60° C. in 2 h, holding 1.0 h at 60° C., cooling from 60° C. to 20° C. in 12 h. After the last cooling to 20° C. the mixture was aged not less than 5 h at 20° C. At 20° C. the suspension was filtered and the crystals were washed twice with 2-propanol (2×50.0 g, 20° C.).

The isolated crystals were dried under vacuum (<100 mbar, at 50° C.) until weight constant. Pure 1b is obtained as white to off-white crystals, designated Form A, in a yield of 84-94%. The product may be delumped to avoid the presence of oversized agglomerates.

All references cited herein are incorporated by reference in their entireties.

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the spirit or scope of the appended claims.

What is claimed:
1. A method of synthesizing a compound of formula 1b, the method comprising:

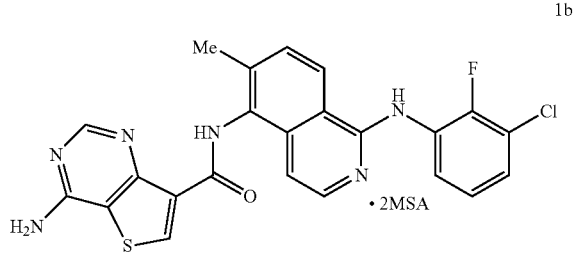 [SMILES: Cc1ccc2c(Nc3cccc(Cl)c3F)nccc2c1NC(=O)c1csc2c(N)ncnc12]

reacting compound 4 with compound 5a to produce compound 6a;

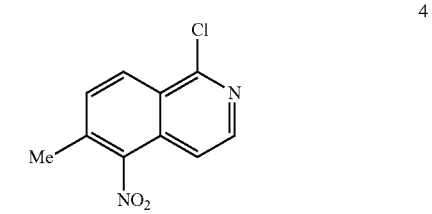

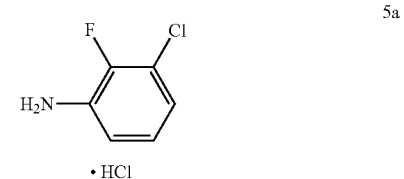

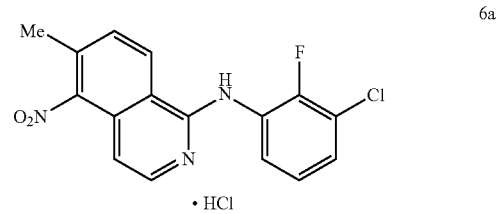

reducing compound 6a with hydrogen over a platinum-vanadium catalyst, with aqueous ammonia, in 2-methyl tetrahydrofuran as a solvent, to form compound 7;

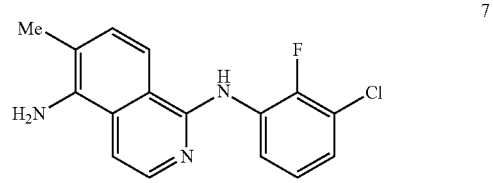

coupling compound 7 with compound 2 using N,N,N',N'-tetramethylchloroformamidinium hexafluorophosphate and 2,6-lutidine, in THF, to produce a THF adduct of compound 1; and

1

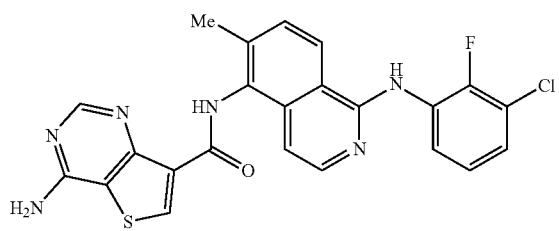

2

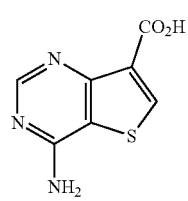

dissolving the THF adduct of compound 1 in an aqueous mixture of methanesulfonic acid in iso-propyl alcohol, to provide a pure form of compound 1b.

2. The method of claim 1 wherein the purity of compound 1b is >99 A % HPLC.

3. The method of claim 1, wherein compound 2 is prepared by a process comprising:
regioselective bromination of compound 22 to produce compound 23;

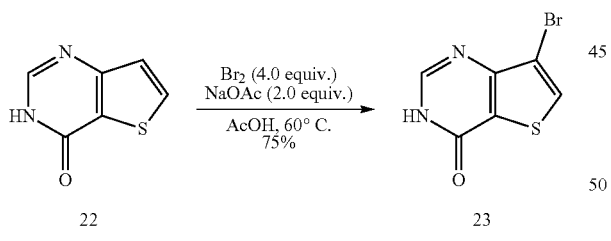

chlorinating compound 23 to form compound 24;

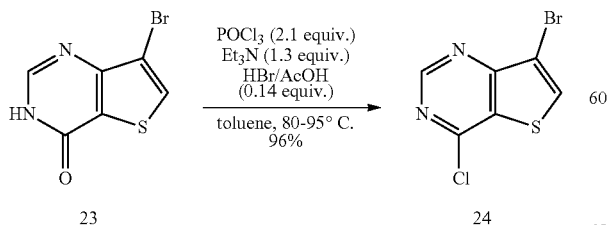

converting compound 24 to a protected compound 25;

 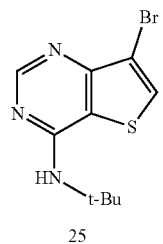

carbonylation of compound 25 to form compound 26;

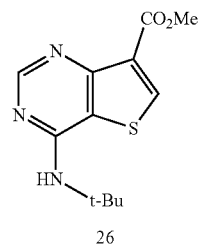

and
deprotecting compound 26 with acid, then base, followed by neutralization with acetic acid to provide compound 2.

4. The method of claim 1 wherein compound 4 is prepared by a process comprising:
selectively methylating 5-nitroisoquinoline to produce compound 42;

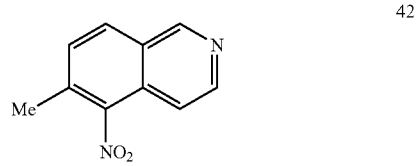 [SMILES: Cc1ccc2cnccc2c1[N+](=O)[O-]]

oxidizing compound 42 to produce compound 43;

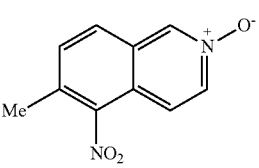

and
chlorinating compound 43 to produce compound 4.

5. The method of claim 1 wherein compound 5a is prepared by a process comprising:

regioselectively fluorinating compound 50 to produce compound 51;

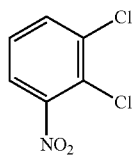

50

51 and catalytically reducing compound 51 with $H_2$ over Raney-nickel to produce compound 5a, wherein the fluorinating and reducing occur in the same reaction vessel without separating compound 51 between each step.

6. The method of claim 1, wherein the reacting compound 4 with compound 5a to produce compound 6a, takes place in methyl ethyl ketone, or in MIBK with $NEt_3$.

7. The method of claim 1, wherein the reducing of compound 6a to form compound 7 takes place via intermediate 6

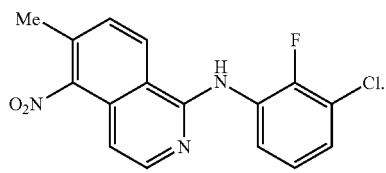

6

8. A method of synthesizing a compound of formula 2, the method comprising:

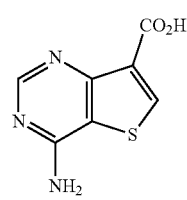

2 reacting compound 20 with compound 21 in methoxy-ethanol to produce compound 22;

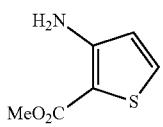

20

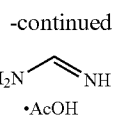

21

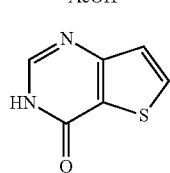

22 brominating compound 22 with dibromine in a sodium acetate buffer to give compound 23;

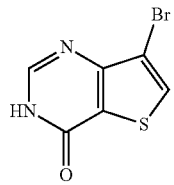

23 converting compound 23 to compound 24 by reaction with $POCl_3$ and $Et_3N$;

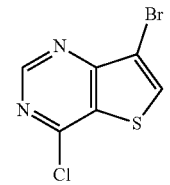

24 aminating compound 24 with $t\text{-BuNH}_2$ to produce compound 25;

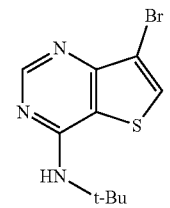

25 converting compound 25 to compound 26 by reaction with (R)-2,2'-bis(diphenylphosphino)-1,1'-binaphthalene in the presence of $Pd(OAc)_2$ in $Et_3N$;

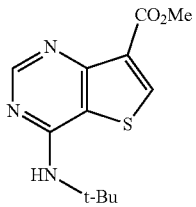

26 and
deprotecting compound 26 with sulfuric acid followed by potassium hydroxide to form compound 2.

9. A method of producing a compound of formula 1 (THF), the method comprising:

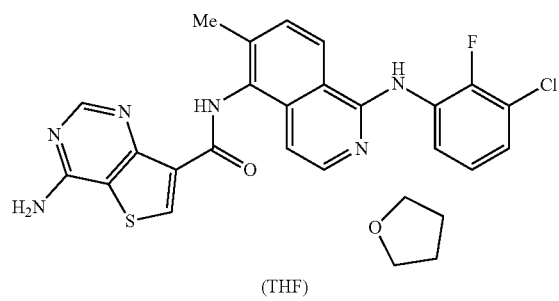

coupling a compound of formula 7 with a compound of formula 2,

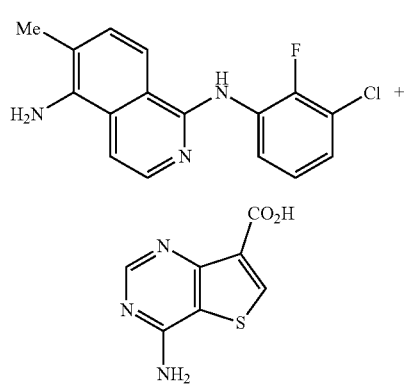

utilizing 2,6-lutidine and TCFH in THF, followed by washing with acetone.

10. A compound of formula:

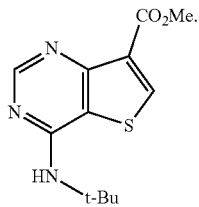 [SMILES: COC(=O)c1csc2c(NC(C)(C)C)ncnc12]

11. A composition comprising a 1:1 adduct of 4-amino-N-(1-((3-chloro-2-fluorophenyl)amino)-6-methylisoquinolin-5-yl)thieno[3,2-d]pyrimidine-7-carboxamide with tetrahydrofuran, or crystalline forms thereof.

12. A method of producing a compound of formula 1b, the method comprising:

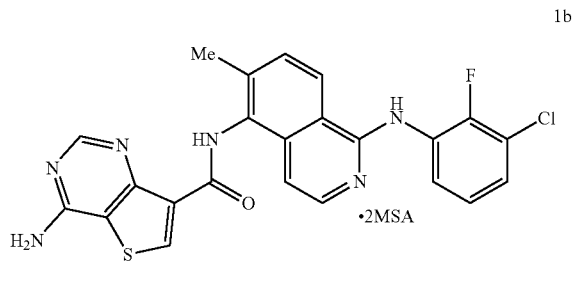 [SMILES: Cc1ccc2c(Nc3cccc(Cl)c3F)nccc2c1NC(=O)c1csc2c(N)ncnc12]

coupling a compound of formula 7 with a compound of formula 2,

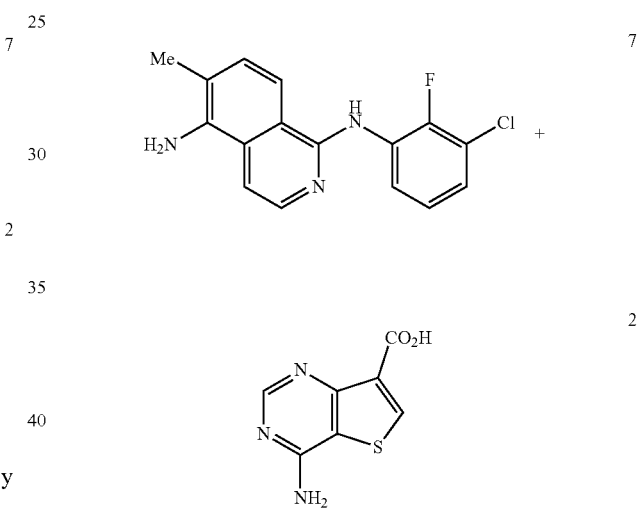

utilizing 2,6-lutidine and TCFH in NMP, followed by washing the product with dimethyl sulphonic acid, in an aqueous mixture of NMP, thereby isolating the compound of formula 1b.

13. The method of claim 12, further comprising:

washing the compound of formula 1b in a mixture of DMSO and dimethylsulfonic acid, followed by recrystallization.

\* \* \* \* \*